(12) United States Patent
Byers et al.

(10) Patent No.: US 9,527,090 B1
(45) Date of Patent: Dec. 27, 2016

(54) MIXED DECYL MERCAPTANS COMPOSITIONS AND USE THEREOF AS MINING CHEMICAL COLLECTORS

(71) Applicant: Chevron Phillips Chemical Company LP, The Woodlands, TX (US)

(72) Inventors: Jim D. Byers, Bartlesville, OK (US); Michael S. Matson, Bartlesville, OK (US); Jason L. Kreider, Copan, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/284,809

(22) Filed: Oct. 4, 2016

Related U.S. Application Data

(62) Division of application No. 14/981,475, filed on Dec. 28, 2015, now Pat. No. 9,505,011.

(51) Int. Cl.
| | |
|---|---|
| *B03D 1/012* | (2006.01) |
| *B03D 1/02* | (2006.01) |
| *C07C 319/00* | (2006.01) |
| *C07C 321/18* | (2006.01) |
| *C07C 319/04* | (2006.01) |
| *C07C 321/04* | (2006.01) |

(52) U.S. Cl.
CPC ............ *B03D 1/012* (2013.01); *C07C 319/04* (2013.01); *C07C 321/04* (2013.01); *C07C 321/18* (2013.01); *B03D 1/02* (2013.01); *B03D 2201/02* (2013.01); *B03D 2203/025* (2013.01)

(58) Field of Classification Search
CPC ....... B03D 1/018; B03D 1/02; B03D 2201/02; B03D 2203/025; C07C 321/04; C07C 321/18; C07C 319/04
See application file for complete search history.

(56) References Cited

U.S. PATENT DOCUMENTS 4,439,314 A * 3/1984 Parlman ................. B03D 1/008
209/166

* cited by examiner

*Primary Examiner* — Thomas M Lithgow
(74) *Attorney, Agent, or Firm* — Conley Rose, P.C.; Rodney B. Carroll; Lynda Jolly

(57) ABSTRACT

Disclosed herein is a process for the recovery of a metal from an ore using a collector composition. The process includes contacting the ore with the collector composition. The collector composition can include sulfur-containing compounds comprising (i) mercaptans comprising branched $C_{10}$ mercaptans compounds selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (ii) sulfides comprising branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

20 Claims, 8 Drawing Sheets

MIXED DECYL MERCAPTANS COMPOSITIONS AND USE THEREOF AS MINING CHEMICAL COLLECTORS

CROSS-REFERENCE TO RELATED APPLICATIONS

This application is a divisional of and claims priority to U.S. patent application Ser. No. 14/981,475 filed Dec. 28, 2015, and entitled "Mixed Decyl Mercaptans Compositions and Use Thereof as Mining Chemical Collectors," which is incorporated by reference herein in its entirety.

TECHNICAL FIELD

The present disclosure relates to compositions containing mixed decyl mercaptans and/or mixed decyl sulfides and use thereof in mining collector compositions. More specifically, the present disclosure relates to compositions containing branched decyl mercaptans and/or branched $C_{20}$ sulfides, and methods of making same.

BACKGROUND

Mercaptans, which are also known as thiols, are organic compounds used in diverse applications. Some mercaptans can be used as precursors for agriculture chemicals or as natural gas additives. While processes for making mercaptans are available, preparing individual mercaptans can be costly due to numerous purification steps required for the feedstock and/or mercaptan product. However, many applications may not require a single pure mercaptan compound, but could utilize mercaptan mixtures. Thus, there is a need to develop mercaptan compositions suitable for such applications, and methods of making same.

One such application is the extraction and recovery of metals from mined ores. In the past, mercaptans such as n-dodecyl mercaptans (NDDM) and tert-dodecyl mercaptans (TDDM) have been used as mining chemical collectors in the extraction and recovery of metals from mined ore. However, NDDM and TDDM have fallen out of favor in the mining industry due to strong odors. Thus, there is an ongoing need for mining chemical collector compositions suitable for metals recovery from mined ore.

BRIEF SUMMARY

Disclosed herein is a process for the recovery of a metal from an ore, the process comprising contacting the ore with a collector composition, wherein the collector composition comprises sulfur-containing compounds, wherein the sulfur-containing compounds comprise (i) mercaptans comprising branched $C_{10}$ mercaptans compounds selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (ii) sulfides comprising branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

Also disclosed herein is a collector composition comprising sulfur-containing compounds. The sulfur-containing compounds comprise (i) mercaptans comprising branched $C_{10}$ mercaptans compounds selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (ii) sulfides comprising branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

BRIEF DESCRIPTION OF THE DRAWINGS

For a detailed description of the preferred embodiments of the disclosed compositions and methods of making same, reference will now be made to the accompanying drawings in which.

DETAILED DESCRIPTION

Figure 1:
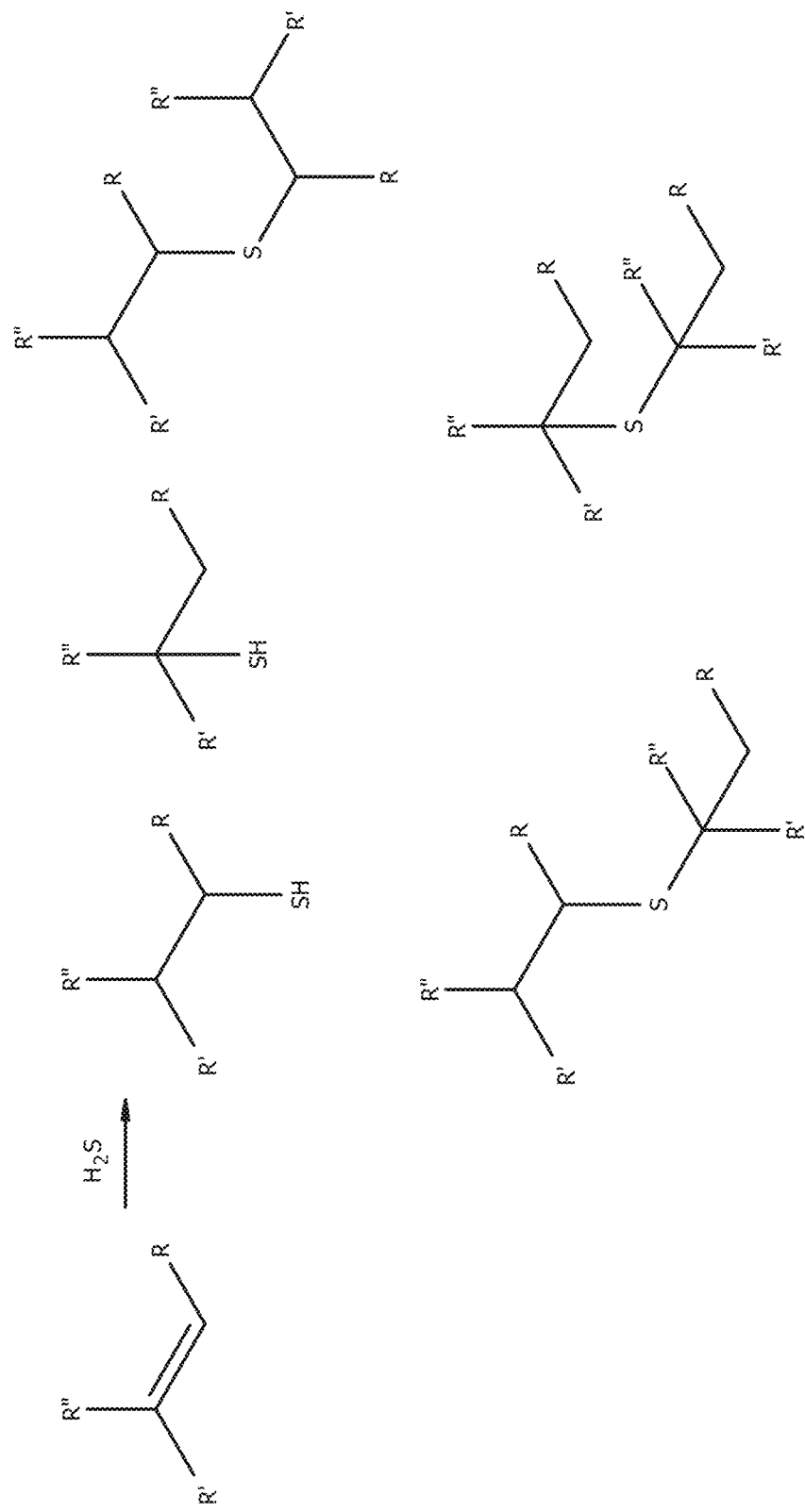
FIG. 1 displays a reaction schematic for addition of hydrogen sulfide ($H_2S$) to an olefin.

To define more clearly the terms used herein, the following definitions are provided. Unless otherwise indicated, the following definitions are applicable to this disclosure. If a term is used in this disclosure, but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News*, 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. The term "consisting essentially of" occupies a middle ground between closed terms like "consisting of" and fully open terms like "comprising." Absent an indication to the contrary, when describing a compound or composition, "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which is utilized and it is possible to have different transitional terms or phrases utilized with different features within a claim. For example, a method can comprise several recited steps (and other non-recited steps), but utilize a catalyst system preparation consisting of specific steps, or alternatively, consisting essentially of specific steps, but utilize a catalyst system comprising recited components and other non-recited components.

While compositions and methods are described in terms of "comprising" (or other broad term) various components and/or steps, the compositions and methods can also be described using narrower terms, such as "consist essentially of" or "consist of" the various components and/or steps.

The terms "a," "an," and "the" are intended, unless specifically indicated otherwise, to include plural alternatives, e.g., at least one.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers, unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers, whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" can formally be derived by removing one hydrogen atom from an alkane, while an "alkylene group" can formally be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure of a substituent, ligand, or other chemical moiety that can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, and tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from a carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms, such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc., such multiple bonds can be identified by use of the term "mono," "di," "tri," etc., within the name. For example, alkamonoenes, alkadienes, and alkatrienes refer to linear or branched acyclic hydrocarbon olefins having only one carbon-carbon double bond (acyclic having a general formula of $C_nH_{2n}$), only two carbon-carbon double bonds (acyclic having a general formula of $C_nH_{2n-2}$), and only three carbon-carbon double bonds (acyclic having a general formula of $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3 position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms.

The terms "lights," "light fraction," or "light compounds" whenever used in this specification and claims refers to compounds present in the reaction product with equal to or less than about 9 carbon atoms ($C_{9-}$) per molecule. Nonlimiting examples of $C_{9-}$ compounds that can be in the reaction product include $C_{9-}$ monoolefins (e.g., unreacted $C_{9-}$ monoolefins), $C_{9-}$ mercaptans, $C_{9-}$ alkanes, $C_{9-}$ alcohols, cyclohexane, methylcyclopentane, methylcyclohexane, benzene, toluene, ethylbenzene, xylene, mesitylene, 2-ethyl-1-hexanol, and the like, or combinations thereof. Unless otherwise specifically indicated herein, the terms "lights," "light fraction," or "light compounds" whenever used in this specification and claims excludes hydrogen sulfide, as $H_2S$ is typically substantially consumed during the preceding reaction and/or removed from the reaction product (as discussed in more detail herein) prior to further processing of the reaction product (e.g., distillation thereof). For example, $H_2S$ can be removed from the reaction product via distillation, stripping, flashing, or other suitable means known to those of skill in the art without removing any substantial amounts of the "lights," "light fraction," or "light compounds" from the reaction product. Not wanting to be limited by theory, this definition of "lights," "light fraction," or "light compounds" includes any compounds with about nine or less carbon atoms present in the reaction product that can be detected, even in trace amounts. As is known to one of skill in the art, the light fraction can also contain trace amounts of lower carbon number sulfides.

The terms "intermediates" or "intermediate fraction" whenever used in this specification and claims typically refers to compounds with about ten to seventeen carbon atoms ($C_{10-17}$) per molecule. Nonlimiting examples of $C_{10-17}$ compounds include $C_{10}$ mercaptans (including both branched and non-branched $C_{10}$ mercaptans), $C_{12-17}$ mercaptan isomers, $C_{12}$-$C_{17}$ sulfides, and the like, or combinations thereof. Not wanting to be limited by theory, this definition of "intermediates" or "intermediate fraction" includes any compounds with about ten to seventeen carbon atoms present in the reaction product that can be detected, even in trace amounts. As is known to one skilled in the art, the intermediate fraction can also contain trace amounts of lower carbon number compounds, including sulfides. In some embodiments, a product can be recovered from the intermediate fraction (e.g., a $C_{10}$ mercaptan fraction), and the remaining $C_{11}$ to $C_{17}$ compounds (e.g., $C_{12-16}$ mercaptans) can be referred to as the intermediate fraction.

The terms "heavies" or "heavy fraction" whenever used in this specification and claims refers to compounds with about eighteen or more carbon atoms ($C_{18+}$) per molecule. Non-limiting examples of $C_{18+}$ products include $C_{18}$ sulfides, $C_{20}$ sulfides, $C_{24}$ sulfides, $C_{28}$ sulfides, $C_{32}$ sulfides, $C_{18}$ mercaptans, and the like, or combinations thereof. As is known to those of skill in the art, the heavy fraction can also contain trace amounts of lower carbon number compounds, including mercaptans and sulfides.

These light, intermediate, and heavy fractions can be referred to as "rough-cuts," in that they contain a plurality of compounds spread across a range of carbon atoms, i.e., a plurality of compounds having a different number of carbon atoms (e.g., a rough cut comprising $C_{10}$, $C_{11}$, $C_{12}$, $C_{13}$, $C_{14}$, $C_{15}$, $C_{16}$, $C_{17}$, etc. compounds). These rough cuts are in contrast to one or more "fine-cuts" that contain a fewer number of compounds than the rough-cuts, for example, a $C_{10}$ fine cut (e.g., a $C_{10}$ mercaptan fraction) derived from or otherwise recovered separately from the rough cut. Accordingly, a rough cut can be comprised of a number of fine cuts, for example where a plurality of cuts are taken via distillation over a period of time and across a ramped temperature range, and referred to collectively as a rough cut or individually as fine cuts. Those of ordinary skill in the art can produce a fine-cut fraction from a rough-cut fraction, for example via further distillation (e.g., a $C_{10}$ splitter, a $C_{20}$ splitter, etc.) or other purification technique.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum value can be alternatively stated as "at least" or "greater than or equal to" any recited minimum value for the feature disclosed herein. Features within this disclosure that are provided as a maximum value can be alternatively stated as "less than or equal to" or "below" any recited maximum value for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms. Moreover, other identifiers or qualifying terms can be utilized to indicate the presence or absence of a particular substituent, a particular regiochemistry and/or stereochemistry, or the presence or absence of a branched underlying structure or backbone.

Processes and/or methods described herein utilize steps, features, and compounds which are independently described herein. The process and methods described herein may or may not utilize step identifiers (e.g., 1), 2), etc., a), b), etc., or i), ii), etc.), features (e.g., 1), 2), etc., a), b), etc., or i), ii), etc.), and/or compound identifiers (e.g., first, second, etc.). However, it should be noted that processes and/or methods described herein can have multiple steps, features (e.g., reagent ratios, formation conditions, among other considerations), and/or multiple compounds having the same general descriptor. Consequently, it should be noted that the processes and/or methods described herein can be modified to use an appropriate step or feature identifier (e.g., 1), 2), etc., a), b), etc., or i), ii), etc.) and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the process and/or methods without detracting from the general disclosure.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

The weight percent compositional aspects of the various compositions described herein (e.g., the weight percent of one or more compounds present in a composition) can be determined by gas chromatography (GC), gas chromatography-mass spectroscopy (GC-MS), Raman spectroscopy, nuclear magnetic resonance (NMR) spectroscopy, or any other suitable analytical method known to those of skill in the art. For example, unless otherwise indicated, the weight percent compositional aspects of the various compositions described herein (e.g., the weight percent of the various sulfur-containing compounds such as $C_{10}$ mercaptans and $C_{20}$ sulfides present in the compositions such as the crude, light fraction, intermediate fraction, heavy faction, etc.) can be determined using a gas chromatograph with a flame ionization detector (GC-FID) detector based on the total GC peak areas (as described herein) and reported as gas chromatography (GC) area percent (GC area %), which is a common analytical technique for compositions comprising sulfur-containing compounds. While not wishing to be bound by this theory, it is believed that the amount in area % is very similar to the amount in weight percent (wt. %), and these respective amounts need not be exactly equivalent or interchangeable in order to be understood by a person of ordinary skill.

In an embodiment, a process of the present disclosure comprises reacting, in a reactor, hydrogen sulfide ($H_2S$) and a feedstock comprising one or more branched $C_{10}$ monoolefins in the presence of an initiating agent to produce a crude composition (also referred to as a crude product); wherein the branched $C_{10}$ monoolefins comprise 5-methyl-1-nonene, 3-propyl-1-heptene, 4-ethyl-1-octene, 2-butyl-1-hexene, or combinations thereof; and wherein the crude composition comprises branched $C_{10}$ mercaptans and branched $C_{20}$ sulfides.

The crude composition can be further processed, for example via distillation, to yield one or more products (also referred to as distilled, purified, refined, finished, or final products) selected from the group consisting of mercaptan compositions (e.g., a composition comprising one or more branched $C_{10}$ mercaptans), sulfide compositions (e.g., a composition comprising one or more branched $C_{20}$ sulfides); and compositions having both mercaptans (e.g., branched $C_{10}$ mercaptans) and sulfides (e.g., branched $C_{20}$ sulfides), referred to as mercaptan/sulfide compositions.

In an embodiment, a mercaptan composition comprises branched $C_{10}$ mercaptans selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof.

In an embodiment, a sulfide composition comprises branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

In an embodiment, a mercaptan/sulfide composition comprises (A) branched $C_{10}$ mercaptans selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (B) branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

The mercaptan compositions, sulfide compositions, and mercaptan/sulfide compositions can be salable or otherwise used for a variety of end uses such as mining ore collector compositions and chain transfer agents.

In an embodiment, the compositions disclosed herein can be prepared by a process comprising reacting, in a reactor, hydrogen sulfide ($H_2S$) and a feedstock comprising one or more branched $C_{10}$ monoolefins in the presence of an initiating agent to produce a crude (reaction product) composition, wherein the branched $C_{10}$ monoolefins comprise 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

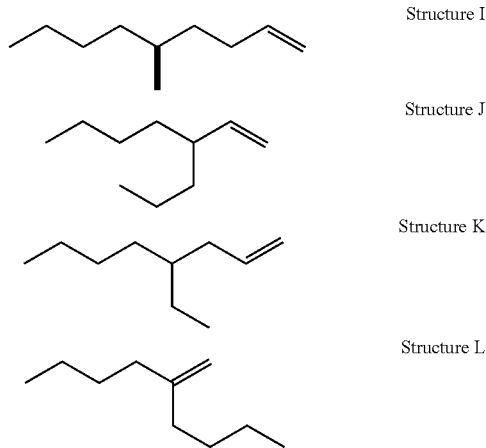

Structure I

Structure J

Structure K

Structure L

Any feedstock comprising one or more branched $C_{10}$ monoolefins of the type described herein can be used, for example a feedstock obtained from a commercial petroleum refining or petrochemical process. Such feedstocks can comprise other olefins in addition to the one or more branched $C_{10}$ monoolefins of the type described herein, for example linear $C_{10}$ monoolefins as well as olefins having more or less than 10 carbon atoms. In an embodiment, the feedstock comprises one or more branched $C_{10}$ monoolefins and is obtained from a 1-hexene production process effluent stream. In various embodiments, a feedstock obtained from a 1-hexene production process effluent stream can comprise $C_{10}$ monoolefins (e.g., branched and/or linear $C_{10}$ monoolefins) as well as olefins having more or less than 10 carbon atoms.

In an embodiment, the feedstock can comprise (a) at least about 76 mol %, alternatively at least about 78 mol %, alternatively at least about 80 mol %, or alternatively at least about 82 mol % $C_{10}$ monoolefins, and (b) at least about 1 mol %, alternatively at least about 2 mol %, alternatively at least about 3 mol %, or alternatively at least about 4 mol % $C_{14}$ monoolefins. In an embodiment, the feedstock can comprise (a) from about 76 mol % to about 92 mol %, alternatively from about 78 mol % to about 90 mol %, alternatively from about 80 mol % to about 88 mol %, or alternatively from about 82 mol % to about 86 mol % $C_{10}$ monoolefins; and (b) from about 1 mol % to about 12 mol %, alternatively from about 2 mol % to about 10 mol %, alternatively from about 3 mol % to about 8 mol %, or alternatively from about 4 mol % to about 7 mol % $C_{14}$ monoolefins. For purposes of the disclosure herein, a feedstock comprising (a) at least about 76 mol % $C_{10}$ monoolefins, and (b) at least about 1 mol % $C_{14}$ monoolefins can also be referred to as a "first feedstock." In an embodiment, the first feedstock is obtained from a 1-hexene production process effluent stream, for example an effluent stream obtained from a 1-hexene production process of the type disclosed in co-pending International Patent Application PCT/US2015/40433, which is incorporated by reference herein in its entirety.

In another embodiment, the feedstock can comprise at least about 95 mol %, alternatively at least about 96 mol %, alternatively at least about 97 mol %, alternatively at least about 98 mol %, or alternatively at least about 99 mol % $C_{10}$ monoolefins. For purposes of the disclosure herein, a feedstock comprising at least about 95 mol % $C_{10}$ monoolefins can also be referred to as a "second feedstock." In an embodiment, the second feedstock can be produced by purifying the first feedstock, such as for example by distillation of an effluent stream obtained from a 1-hexene production process of the type disclosed in co-pending International Patent Application PCT/US2015/40433, which is incorporated by reference herein in its entirety.

In an embodiment, the $C_{10}$ monoolefins of any feedstock described herein (e.g., a first feedstock or a second feedstock) can comprise, can consist essentially of, or can be, 2-butyl-1-hexene, 3-propyl-1-heptene, 4-ethyl-1-octene, and 5-methyl-1-nonene. In an embodiment, the $C_{10}$ monoolefins of any feedstock described herein can comprise i) at least about 3 mol %, alternatively at least about 4 mol %, alternatively at least about 5 mol %, alternatively at least about 6 mol %, alternatively at least about 7 mol %, or alternatively at least about 8 mol % 2-butyl-1-hexene (represented by Structure L), ii) at least about 8 mol %, alternatively at least about 9 mol %, alternatively at least about 10 mol %, alternatively at least about 11 mol %, alternatively at least about 12 mol %, or alternatively at least about 13 mol % 3-propyl-1-heptene (represented by Structure J), iii) at least about 6 mol %, alternatively at least about 7 mol %, alternatively at least about 8 mol %, alternatively at least about 9 mol %, alternatively at least about 10 mol %, or alternatively at least about 11 mol % 4-ethyl-1-octene (represented by Structure K), and iv) at least about 20 mol %, alternatively at least about 22 mol %, alternatively at least about 24 mol %, alternatively at least about 26 mol %, alternatively at least about 28 mol %, or alternatively at least about 30 mol % 5-methyl-1-nonene (represented by Structure I).

In an embodiment, the $C_{10}$ monoolefins of any feedstock described herein (e.g., a first feedstock or a second feedstock) can have a molar ratio of 2-butyl-1-hexene to 5-methyl-1-nonene of at least about 2:1, alternatively at least about 2.4:1, alternatively at least about 2.6:1, or alternatively at least about 2.8:1. In an embodiment, the $C_{10}$ monoolefins of any feedstock described herein can have a molar ratio of 3-propyl-1-heptene to 5-methyl-1-nonene of at least about 1.2:1, alternatively at least about 1.4:1, alternatively at least about 1.6:1, or alternatively at least about 1.8:1. In an embodiment, the $C_{10}$ monoolefins of any feedstock described herein can have a molar ratio of 4-ethyl-1-octene to 5-methyl-1-nonene of at least about 1.6:1, alternatively at least about 1.7:1, alternatively at least about 1.9:1, or alternatively at least about 2.1:1. In an embodiment, the $C_{10}$ monoolefins of any feedstock described herein can have a molar ratio of 2-butyl-1-hexene to 5-methyl-1-nonene of at least about 2:1, alternatively at least about 2.4:1, alternatively at least about 2.6:1, or alternatively at least about 2.8:1; a molar ratio of 3-propyl-1-heptene to 5-methyl-1-nonene of at least about 1.2:1, alternatively at least about 1.4:1, alternatively at least about 1.6:1, or alternatively at least about 1.8:1; and a molar ratio of 4-ethyl-1-octene to 5-methyl-1-nonene of at least about 1.6:1, alternatively at least about 1.7:1, alternatively at least about 1.9:1, or alternatively at least about 2.1:1.

In an embodiment, the $C_{10}$ monoolefins of any feedstock described herein (e.g., a first feedstock or a second feedstock) can comprise linear $C_{10}$ monoolefins. In such embodiment, the linear $C_{10}$ monoolefins can comprise, can consist essentially of, or can be, 1-decene, 4-decene, 5-decene, or combinations thereof; alternatively, 1-decene; alternatively, 4-decene and/or 5-decene; alternatively, 4-decene; or alternatively, 5-decene. In an embodiment, the $C_{10}$ monoolefins of any feedstock described herein can comprise less than or equal to about 26 mol %, alternatively less than or equal to about 24 mol %, alternatively less than or equal to about 22 mol %, alternatively less than or equal to about 20 mol %, or alternatively less than or equal to about 18 mol % linear $C_{10}$ monoolefins. In an embodiment, the $C_{10}$ monoolefins of any feedstock described herein can comprise from about 1 mol % to about 16 mol %, alternatively from about 2 mol % to about 15 mol %, alternatively from about 3 mol % to about 14 mol %, alternatively from about 4 mol % to about 13 mol %, or alternatively from about 6 mol % to about 12 mol % 4-decene and/or 5-decene. In some embodiments, the $C_{10}$ monoolefins of any feedstock described herein can comprise less than or equal to about 10 mol %, alternatively less than or equal to about 9 mol %, alternatively less than or equal to about 8 mol %, alternatively less than or equal to about 7 mol %, or alternatively less than or equal to about 6 mol % 1-decene. In other embodiments, the $C_{10}$ monoolefins of any feedstock described herein can comprise from about 0.5 mol % to about 9 mol %, alternatively from about 1 mol % to about 8 mol %, alternatively from about 1.5 mol % to about 7 mol %, or alternatively from about 2 mol % to about 6 mol % 1-decene.

In an embodiment, the first feedstock disclosed herein can further comprise $C_{9-}$ monoolefins, $C_{11+}$ monoolefins, or combinations thereof; alternatively, $C_{9-}$ monoolefins; or alternatively, $C_{11+}$ monoolefins. In an embodiment, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins can comprise, can consist essentially of, or can be, a $C_8$ monoolefin. In an embodiment, the $C_{11+}$ monoolefins can comprise, can consist essentially of, or can be, a $C_{11}$ monoolefin, a $C_{12}$ monoolefin, a $C_{13}$ monoolefin, a $C_{14}$ monoolefin, a $C_{15}$ monoolefin, a $C_{16}$ monoolefin, a $C_{17}$ monoolefin, a $C_{18}$ monoolefin, or combinations thereof; alternatively, a $C_{11}$ monoolefin; alternatively, a $C_{12}$ monoolefin; alternatively, a $C_{13}$ monoolefin; alternatively, a $C_{14}$ monoolefin; alternatively, a $C_{15}$ monoolefin; alternatively, a $C_{16}$ monoolefin; alternatively, a $C_{17}$ monoolefin; or alternatively, a $C_{18}$ monoolefin. In some embodiments, the $C_{11+}$ monoolefins can comprise, can consist essentially of, or can be, a $C_{12}$ monoolefin, a $C_{16}$ monoolefin, a $C_{18}$ monoolefin, or combinations thereof; alternatively, a $C_{12}$ monoolefin; alternatively, a $C_{16}$ monoolefin; or alternatively, a $C_{18}$ monoolefin.

In an embodiment, the first feedstock disclosed herein can further comprise $C_8$ monoolefins, $C_{12}$ monoolefins, $C_{16}$ monoolefins, $C_{18}$ monoolefins, or combinations thereof; alternatively, $C_8$ monoolefins; alternatively, $C_{12}$ monoolefins; alternatively, $C_{16}$ monoolefins and/or $C_{18}$ monoolefins; alternatively, $C_{16}$ monoolefins; or alternatively, $C_{18}$ monoolefins. In an embodiment, the $C_8$ monoolefins can comprise 1-octene. In an embodiment, the $C_{12}$ monoolefins can comprise 1-dodecene.

In an embodiment, the first feedstock can further comprise from about 0.1 mol % to about 5 mol %, alternatively from about 0.25 mol % to about 4 mol %, or alternatively from about 0.5 mol % to about 3 mol % $C_{12}$ monoolefins. In such embodiment, the $C_{12}$ monoolefins can comprise from about 54 mol % to about 74 mol %, alternatively from about 56 mol % to about 72 mol %, alternatively from about 58 mol % to about 70 mol %, or alternatively from about 60 mol % to about 68 mol % 1-dodecene.

In an embodiment, the first feedstock can further comprise from about 0.1 mol % to about 5 mol %, alternatively from about 0.25 mol % to about 4 mol %, or alternatively from about 0.5 mol % to about 3 mol % $C_8$ monoolefins. In such embodiment, the $C_8$ monoolefins can comprise at least about 95 mol %, alternatively at least about 96 mol %, alternatively at least about 97 mol %, alternatively at least about 98 mol %, or alternatively at least about 99 mol % 1-octene.

In an embodiment, the first feedstock can further comprise from about 0.05 mol % to about 2 mol %, alternatively from about 0.04 mol % to about 1.5 mol %, alternatively from about 0.06 mol % to about 1.25 mol %, alternatively from about 0.08 mol % to about 1 mol %, or alternatively from about 0.1 mol % to about 0.75 mol % $C_{16}$ monoolefins and/or $C_{18}$ monoolefins.

In an embodiment, a feedstock comprising branched $C_{10}$ monoolefins produced in a 1-hexene process can be purified to produce a second feedstock of the type described herein, for example to improve olefin reactivity and resultant mercaptan and/or sulfide purity. A light fraction, comprising $C_{9-}$, can be removed from the feedstock and any $C_{10}$ olefin isomers can be collected overhead to obtain a high purity (>95%) $C_{10}$ monoolefin fraction as the second feedstock. This high purity $C_{10}$ monoolefin fraction (i.e., second feedstock) comprises little or no non-olefin impurities or $C_{11}$ to $C_{17}$ compounds. The high purity $C_{10}$ olefin can be reacted with $H_2S$ to produce a crude composition. Reaction conditions to produce a crude composition from the high purity $C_{10}$ monoolefin fraction (i.e., a second feedstock) can be identical to the reaction conditions disclosed for the feedstock comprising branched $C_{10}$ monoolefins produced in a 1-hexene process used as received without further purification (i.e., a first feedstock). The major difference between reacting a first feedstock and a second feedstock is the composition of the crude composition and any resulting purified or partially purified products (e.g., fractions or cuts taken from the crude composition). For the second feedstock (e.g., a high purity (>95%) $C_{10}$ monoolefin fraction), the crude composition can comprise residual $H_2S$, unreacted $C_{10}$ olefin, $C_{10}$ mercaptan isomers, and $C_{10}H_{21}$—S—$C_{10}H_{21}$ sulfides and minimal other mercaptans or sulfides. After removal of $H_2S$ and $C_{9-}$ lights from the crude composition, the resultant partially purified product will contain $C_{10}$ mercaptan isomers and $C_{20}$ sulfides, but will not contain any of the intermediate mercaptans and asymmetric sulfide components formed by reactions of olefins having less than or greater than 10 carbon atoms (because there were minimal, if any, such olefins having less than or greater than 10 carbon atoms in the purified feedstock). While not wishing to be bound by theory, it is believed that the intermediate mercaptans and asymmetric sulfide components can be produced from the reaction of $C_{10}$ mercaptans with other non-$C_{10}$ olefins.

In an embodiment, $H_2S$ and a feedstock comprising one or more branched $C_{10}$ monoolefins can be reacted at an $H_2S$ to olefin molar ratio of from about 1:1 to about 20:1, alternatively from about 2:1 to about 15:1, or alternatively from about 3:1 to about 10:1.

In an embodiment, $H_2S$ and a feedstock comprising one or more branched $C_{10}$ monoolefins can be reacted at a pressure of from about 30 psig (206 kPag) to about 1,500 (10,300 kPag) psig, alternatively from about 100 psig (690 kPag) to about 1,250 psig (8,600 kPag), or alternatively from about 250 (1,700 kPag) psig to about 1,000 psig (6,900 kPag).

In an embodiment, $H_2S$ and a feedstock comprising one or more branched $C_{10}$ monoolefins can be reacted to produce olefin conversion of equal to or greater than about 80%, alternatively equal to or greater than about 85%, or alternatively equal to or greater than about 90%. For purposes of the disclosure herein, an olefin conversion refers to the mol % of olefins that have reacted during the reaction between $H_2S$ and a feedstock in a reactor, with respect to the amount of olefins introduced into the reactor during the same time period.

In an embodiment, the process can comprise reacting $H_2S$ and a feedstock (e.g., a first or second feedstock as described herein) comprising one or more branched $C_{10}$ monoolefins in the presence of an initiating agent to produce a crude composition; wherein the initiating agent comprises ultraviolet (UV) radiation. In such embodiment, the UV radiation can be any UV radiation capable of initiating the reaction of the olefins present in the feedstock and $H_2S$. In some embodiments, the UV radiation can be generated by a medium pressure mercury lamp. As will be appreciated by one of skill in the art, and with the help of this disclosure, although UV radiation can be the initiating agent, other suitable types of light sources can be used.

In an embodiment, $H_2S$ and a feedstock comprising one or more branched $C_{10}$ monoolefins can be reacted in the presence of an initiating agent comprising UV radiation in a batch reactor or a continuous reactor. Nonlimiting examples of continuous reactors suitable for use in the present disclosure include continuous flow reactors, continuous stirred reactors, fixed bed reactors, and the like, or combinations thereof. Nonlimiting examples of batch reactors suitable for use in the present disclosure include UV batch reactors. As will be appreciated by one of skill in the art, and with the help of this disclosure, any other suitable type of batch and continuous reactors can be used for reacting $H_2S$ and a feedstock comprising one or more branched $C_{10}$ monoolefins in the presence of UV radiation. UV reactors and conditions suitable for reacting $H_2S$ and a feedstock comprising one or more branched $C_{10}$ monoolefins in the presence of UV radiation are described in more detail in U.S. Pat. No. 7,989,655, and U.S. Publication No. 20140221692 A1, each of which is incorporated by reference herein in its entirety.

In embodiments where $H_2S$ and a feedstock comprising one or more branched $C_{10}$ monoolefins are reacted in the presence of UV radiation in a continuous reactor, the continuous reactor can be sized and configured to the desired continuous production rate. That is, a person skilled in the art will be able to select an appropriate reaction vessel size, geometry and material (e.g., a transparent material for sidewalls, windows, or internal chambers); along with an appropriate number of UV sources; and arrange the sources and reactor vessel (e.g., place UV sources adjacent a transparent exterior portion of the reaction vessel and/or disposed in transparent chambers within the reactor vessel) to yield a desired continuous production rate.

In embodiments where $H_2S$ and a feedstock comprising one or more branched $C_{10}$ monoolefins are reacted in the presence of UV radiation in a batch reactor, the batch reactor can be characterized by a reaction time of from about 1 minute to about 4 hours, alternatively from about 10 minutes to about 2 hours, or alternatively from about 30 minutes to about 1.5 hours.

In an embodiment, $H_2S$ and a feedstock comprising one or more branched $C_{10}$ monoolefins can be reacted in the presence of UV radiation at a temperature of from about 0°

C. to about 100° C., alternatively from about 10° C. to about 70° C., or alternatively from about 15° C. to about 35° C.

In an embodiment, $H_2S$ and a feedstock comprising one or more branched $C_{10}$ monoolefins can be reacted in the presence of UV radiation at a $H_2S$ to olefin molar ratio of from about 1:1 to about 15:1, alternatively from about 2:1 to about 12.5:1, or alternatively from about 5:1 to about 10:1.

In an embodiment, the process can comprise reacting $H_2S$ and a feedstock comprising one or more branched $C_{10}$ monoolefins in the presence of an initiating agent to produce a crude composition; wherein the initiating agent comprises ultraviolet (UV) radiation, and wherein the initiating agent further comprises a phosphite promoter, a photoinitiator, or both.

In an embodiment, the phosphite promoter can be used in an amount of from about 0.01 wt. % to about 5 wt. %, alternatively from about 0.1 wt. % to about 4 wt. %, or alternatively from about 1 wt. % to about 2.5 wt. %, based on a weight of olefins.

In an embodiment, the phosphite promoter can be characterized by formula $P(OR^5)_3$, wherein each $R^5$ can independently be a $C_1$-$C_{18}$ hydrocarbyl group, alternatively $C_1$-$C_{10}$ hydrocarbyl group, alternatively $C_1$-$C_5$ hydrocarbyl group; alternatively a $C_1$-$C_{18}$ alkyl group, alternatively $C_1$-$C_{10}$ alkyl group, alternatively $C_1$-$C_5$ alkyl group; alternatively, a $C_6$-$C_{18}$ aryl group, or alternatively, a $C_6$-$C_{10}$ aryl group. Nonlimiting examples of $R^5$ groups suitable for use in the present disclosure in the phosphite promoter include a methyl group, an ethyl group, a propyl group, a butyl group, a pentyl group, a hexyl group, a heptyl group, an octyl group, a nonyl group, a decyl group; a phenyl group, a tolyl group, a xylyl group, a naphthyl group; and the like, or combinations thereof.

Nonlimiting examples of phosphite promoters suitable for use in the present disclosure include a trialkylphosphite, trimethylphosphite, triethylphosphite, tributylphosphite; a triarylphosphite, triphenylphosphite; and the like, or combinations thereof.

In an embodiment, the photoinitiator can be used in an amount of from about 0.05 wt. % to about 5 wt. %, alternatively from about 0.1 wt. % to about 4 wt. %, or alternatively from about 1 wt. % to about 2.5 wt. %, based on the weight of olefins present in the feed mixture.

Nonlimiting examples of photoinitiators suitable for use in the present disclosure include 1-hydroxy-cyclohexyl-phenyl-ketone, benzophenone, Bis-(2,4,6-trimethylbenzoyl)-phenylphosphineoxide, 2-hydroxy-1-{4-[4-(2-hydroxy-2-methyl-propionyl)-benzyl]-phenyl}-2-methy-1-propan-1-one, 2-hydroxy-2-methyl-1-phenyl-1-propanone, and the like, or combinations thereof.

In an embodiment, the process can comprise reacting $H_2S$ and a feedstock comprising one or more branched $C_{10}$ monoolefins in the presence of UV radiation to produce a crude composition (wherein the crude composition comprises from 50-100 wt. % $C_{10}$ mercaptans, alternatively from 50-90 wt. % $C_{10}$ mercaptans, alternatively from 75-85 wt. % $C_{10}$ mercaptans); wherein the $C_{10}$ mercaptans present in the crude composition further comprise from about 70 wt. % to about 100 wt. %, alternatively from about 70 wt. % to about 95 wt. %, alternatively from about 80 wt. % to about 90 wt. %, or alternatively from about 79 wt. % to about 85 wt. % $C_{10}$ primary mercaptans; from about 0 wt. % to about 30 wt. %, alternatively from about 0 wt. % to about 20 wt. %, alternatively from about 10 wt. % to about 20 wt. %, or alternatively from about 5 wt. % to about 19 wt. % $C_{10}$ secondary mercaptans; and from about 0 wt. % to about 10 wt. %, alternatively from about 0 wt. % to about 5 wt. %, or alternatively from about 0 wt. % to about 3 wt. % $C_{10}$ tertiary mercaptans. For purposes of the disclosure herein, a primary mercaptan is a mercaptan that has the thiol group (—SH) attached to a primary carbon (e.g., a carbon atom that is attached to one and only one other carbon atom). Further, for purposes of the disclosure herein, a secondary mercaptan is a mercaptan that has the thiol group (—SH) attached to a secondary carbon (e.g., a carbon atom that is attached to two and only two other carbon atoms). Further, for purposes of the disclosure herein, a tertiary mercaptan is a mercaptan that has the thiol group (—SH) attached to a tertiary carbon (e.g., a carbon atom that is attached to three and only three other carbon atoms). As will be appreciated by one of skill in the art, and with the help of this disclosure, the make-up of the crude composition, in terms of primary, secondary, and tertiary mercaptans, will depend on the make-up of the feedstock, as well as on the reaction conditions. Further, as will be appreciated by one of skill in the art, and with the help of this disclosure, the make-up of each of the primary, secondary, and tertiary mercaptans will depend on the make-up of the feedstock, as well as on the reaction conditions.

In an embodiment, the $C_{10}$ primary mercaptans can comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 1-mercapto-decane (represented by Structure M), or combinations thereof.

In an embodiment, the $C_{10}$ secondary mercaptans can comprise 4-mercapto-decane (represented by Structure N), 5-mercapto-decane (represented by Structure O), 5-methyl-2-mercapto-nonane (represented by Structure E), 3-propyl-2-mercapto-heptane (represented by Structure F), 4-ethyl-2-mercapto-octane (represented by Structure G), 2-mercapto-decane (represented by Structure P), or combinations thereof.

In an embodiment, the $C_{10}$ tertiary mercaptans can comprise equal to or greater than about 90 wt. %, alternatively equal to or greater than about 95 wt. %, or alternatively equal to or greater than about 99 wt. % 5-methyl-5-mercapto-nonane (represented by Structure H).

In an embodiment, the process can comprise reacting $H_2S$ and a feedstock (e.g., a first or second feedstock as described herein) comprising one or more branched $C_{10}$ monoolefins in the presence of an initiating agent (e.g., catalyst) to produce a crude composition; wherein the initiating agent comprises an acid catalyst. Nonlimiting examples of acid catalysts suitable for use in the present disclosure include acid washed clays (such as, but not limited to, Filtrol® 24 or Filtrol® 24X); acid washed bentonite; a tetrafluoroethylene polymer resin modified with perfluorovinyl ether groups terminated with sulfonate groups; a macroreticular, sulfonated, crosslinked copolymer of styrene and divinyl benzene; and the like, or combinations thereof.

In an embodiment, $H_2S$ and a feedstock comprising one or more branched $C_{10}$ monoolefins can be reacted in the presence of an acid catalyst in a continuous reactor, such as for example continuous flow reactor, continuous stirred reactors, fixed bed reactors, packed bed reactors, and the like, or combinations thereof.

In embodiments where $H_2S$ and a feedstock comprising one or more branched $C_{10}$ monoolefins are reacted in the presence of an acid catalyst in a continuous reactor, the continuous reactor can be characterized by a weight hourly space velocity (WHSV) of from about 0.1 $h^{-1}$ to about 5 $h^{-1}$, alternatively from about 0.5 $h^{-1}$ to about 4 $h^{-1}$, or alternatively from about 1 h$^{-1}$ to about 3 h$^{-1}$, based on mass of olefin per mass of catalyst per hour.

In an embodiment, H$_2$S and a feedstock comprising one or more branched C$_{10}$ monoolefins can be reacted in the presence of an acid catalyst at a temperature of from about 100° C. to about 300° C., alternatively from about 120° C. to about 220° C., or alternatively from about 180° C. to about 200° C.

In an embodiment, H$_2$S and a feedstock comprising one or more branched C$_{10}$ monoolefins can be reacted in the presence of an acid catalyst at a H$_2$S to olefin molar ratio of from about 1:1 to about 10:1, alternatively from about 2:1 to about 7.5:1, or alternatively from about 2.5:1 to about 5:1.

In an embodiment, the process can comprise reacting H$_2$S and a feedstock comprising one or more branched C$_{10}$ monoolefins in the presence of an acid catalyst to produce a crude composition (wherein the crude composition comprises from 50-100 wt. % C$_{10}$ mercaptans, alternatively from 50-90 wt. % C$_{10}$ mercaptans, alternatively from 75-85 wt. % C$_{10}$ mercaptans); wherein the C$_{10}$ mercaptans comprise from about 0 wt. % to about 5 wt. % alternatively from about 0.1 wt. % to about 4 wt. %, or alternatively from about 0.5 wt. % to about 2.5 wt. % C$_{10}$ primary mercaptans; from about 80 wt. % to about 95 wt. %, alternatively from about 82.5 wt. % to about 92.5 wt. %, or alternatively from about 85 wt. % to about 90 wt. % C$_{10}$ secondary mercaptans; and from about 5 wt. % to about 20 wt. %, alternatively from about 7.5 wt. % to about 17.5 wt. %, or alternatively from about 10 wt. % to about 15 wt. % C$_{10}$ tertiary mercaptans.

In an embodiment, the process can comprise reacting H$_2$S and a feedstock (e.g., a first or second feedstock as described herein) comprising one or more branched C$_{10}$ monoolefins in the presence of an initiating agent to produce a crude composition; wherein the initiating agent comprises a hydrodesulfurization (HDS) catalyst.

In an embodiment, the HDS catalyst comprises a comprises a metal, a transition metal, Ru, Co, Mo, Ni, W, sulfides thereof, disulfides thereof, and the like, or combinations thereof.

In an embodiment, the HDS catalyst can be Haldor Topsoe TK-554 or TK-570, and the like, or combinations thereof.

In an embodiment, the HDS catalyst can further comprise a support, such as for example alumina, silica, and the like, or combinations thereof.

In an embodiment, H$_2$S and a feedstock comprising one or more branched C$_{10}$ monoolefins can be reacted in the presence of an HDS catalyst in a continuous reactor, such as for example continuous flow reactor, continuous stirred reactors, fixed bed reactors, packed bed reactors, and the like, or combinations thereof.

In embodiments where H$_2$S and a feedstock comprising one or more branched C$_{10}$ monoolefins are reacted in the presence of an HDS catalyst in a continuous reactor, the continuous reactor can be characterized by a WHSV of from about 0.1 h$^{-1}$ to about 5 h$^{-1}$, alternatively from about 0.5 h$^{-1}$ to about 4 h$^{-1}$, or alternatively from about 1 h$^{-1}$ to about 3 h$^{-1}$, based on mass of olefin per mass of catalyst per hour.

In an embodiment, H$_2$S and a feedstock comprising one or more branched C$_{10}$ monoolefins can be reacted in the presence of an HDS catalyst at a temperature of from about 100° C. to about 300° C., alternatively from about 120° C. to about 220° C., or alternatively from about 180° C. to about 200° C.

In an embodiment, H$_2$S and a feedstock comprising one or more branched C$_{10}$ monoolefins can be reacted in the presence of an HDS catalyst at a H$_2$S to olefin molar ratio of from about 1:1 to about 10:1, alternatively from about 2:1 to about 7.5:1, or alternatively from about 2.5:1 to about 5:1.

In an embodiment, the process can comprise reacting H$_2$S and a feedstock comprising one or more branched C$_{10}$ monoolefins in the presence of an HDS catalyst to produce a crude composition (wherein the crude composition comprises from 50-100 wt. % C$_{10}$ mercaptans, alternatively from 50-90 wt. % C$_{10}$ mercaptans, alternatively from 75-85 wt. % C$_{10}$ mercaptans); wherein the C$_{10}$ mercaptans comprise from about 5 wt. % to about 30 wt. % alternatively from about 10 wt. % to about 25 wt. %, or alternatively from about 15 wt. % to about 20 wt. % C$_{10}$ primary mercaptans; from about 60 wt. % to about 75 wt. %, alternatively from about 62.5 wt. % to about 72.5 wt. %, or alternatively from about 65 wt. % to about 70 wt. % C$_{10}$ secondary mercaptans; and from about 5 wt. % to about 15 wt. %, alternatively from about 7.5 wt. % to about 13.5 wt. %, or alternatively from about 9 wt. % to about 12 wt. % C$_{10}$ tertiary mercaptans.

As noted previously, any such feedstocks comprising one or more branched C$_{10}$ monoolefins can be reacted with hydrogen sulfide (H$_2$S) in the presence of an initiating agent to produce a crude composition, and the crude composition can be further refined (e.g., distilled or otherwise separated into one or more fractions such as lights, intermediate, and heavies) to yield the various compositions described herein. As described in more detail herein, the type and/or amounts of the constituent components that form the crude composition can vary depending upon the feedstock (e.g., the amount and types of olefins therein), the reaction conditions, the catalysts employed, etc., and one skilled in the art can tailor the post reactor processing of the crude composition to account for the specific compounds present in a given crude composition to yield various desired products and compositions of the types described herein.

Upon completion of the reaction of a feedstock comprising one or more branched C$_{10}$ monoolefins with hydrogen sulfide (H$_2$S), a reactor effluent can be recovered from the reactor and H$_2$S removed therefrom to yield a crude composition. The term "crude composition" or "crude product" refers to an unrefined effluent stream recovered from the reactor after removal of H$_2$S, and in particular to an H$_2$S-free effluent stream that has not undergone any additional post-reactor processing such as flashing, distillation, or other separation techniques or processes to remove any components from the effluent stream other than the initial removal of H$_2$S.

Hydrogen sulfide (H$_2$S) is a highly corrosive, poisonous, flammable, explosive gas. As such, it is typically removed before the crude composition can be further processed or utilized. Bulk H$_2$S can be removed under conditions of reduced pressure, and residual H$_2$S can be removed at reduced temperature and pressure without removing any substantial quantities of the lights. Alternatively, H$_2$S can also be removed by sparging inert gas into the liquid phase. Alternatively, there are other methods for removing H$_2$S (i.e., absorption, stripping, etc.) that are known to those of skill in the art. In an embodiment, under appropriate conditions, a reactor effluent can be treated to remove essentially all of any excess and/or unreacted hydrogen sulfide (H$_2$S).

The crude composition comprises branched C$_{10}$ mercaptans and branched C$_{20}$ sulfides formed by the reaction of H$_2$S and the one or more branched C$_{10}$ monoolefins, and the structures of these branched C$_{10}$ mercaptans and branched C$_{20}$ sulfides are described in more detail herein. In addition to branched C$_{10}$ mercaptans and branched C$_{20}$ sulfides, the crude composition can comprise a number of other compounds such as unreacted olefins, inert compounds (e.g., alkanes), non-branched $C_{10}$ mercaptans, non-branched $C_{20}$ sulfides, non-$C_{10}$ mercaptans, non-$C_{20}$ sulfides, and other impurities. The constituent components contained within the crude composition can vary depending upon the composition of the feedstock (e.g., an unpurified first feedstock as compared to a purified second feedstock as described herein) as well as reaction conditions, catalyst, etc. In various embodiments, a crude composition can comprise light, intermediate, and heavy fractions as described herein.

In an embodiment, the crude compositions can contain a variety of other non-$C_{10}$ mercaptan and non-$C_{20}$ sulfides components (e.g., impurities) such as $C_8$ mercaptans; $C_{12}$ mercaptans; $C_{14}$ mercaptans; $C_{16}$ mercaptans; $C_{18}$ mercaptans; $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; unreacted $C_{8-18}$ monoolefins; non-olefin impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate; and combinations thereof.

In an embodiment, a crude composition comprising branched $C_{10}$ mercaptans and branched $C_{20}$ sulfides can be separated by any process or unit operation known in the art. For example, a crude composition can be processed (e.g., distilled) to remove a fraction of light compounds. Alternatively, a crude composition can be processed to recover both a lights fraction and an intermediates fraction (e.g., a rough cut), followed by further processing to obtain one or more fine cuts. Alternatively, a crude composition can be processed to recover a heavies fraction (e.g., a $C_{20}$ sulfide fraction). Alternatively, a crude composition can be processed to separate out any combination of a lights fraction, an intermediates fraction (e.g., comprising $C_{10}$ mercaptans, including branched $C_{10}$ mercaptans), and a heavies fraction (e.g., comprising $C_{20}$ sulfides, including branched $C_{20}$ sulfides). Furthermore, a light, intermediate or heavy fraction (e.g., a rough cut) can be further processed or parsed to obtain one or more desired fine cuts (e.g., a $C_{10}$ mercaptan fraction). Alternatively, a crude composition can be separated to produce a high-purity $C_{10}$ mercaptan stream and/or a high-purity $C_{20}$ sulfide stream (e.g., to obtain a desired fine cut or fraction such as a $C_{10}$ mercaptan fraction). Further, these separated streams can be blended in any combination of ratios to produce a mixture with specific concentrations of one of more components (e.g., desired blend ratios of branched $C_{10}$ mercaptans and/or branched $C_{20}$ sulfides, for example to aid in a particular end use). The unit operations/processes used for these separations are known to one of skill and the art and include, but are not limited to, distillation, fractionation, flashing, stripping, and absorption, and others. The unit operation conditions, such as for example, temperature, pressure, flow rates, and others at which these unit operations produce one or more of the desired fractions can easily be determined by one of ordinary skill in the art.

In an embodiment, a lights fraction is removed from the crude composition, for example by flashing, distillation, fractionation, stripping, absorption, etc.

In an embodiment, the lights fraction can comprise at least about 90 wt. %, alternatively at least about 90 wt. %, alternatively at least about 95 wt. %, alternatively at least about 96 wt. %, alternatively at least about 97 wt. %, alternatively at least about 98 wt. %, alternatively at least about 99 wt. % $C_{9-}$ compounds, based on the total weight of the lights fraction. Nonlimiting examples of $C_{9-}$ compounds include $C_{9-}$ monoolefins (e.g., unreacted $C_{9-}$ monoolefins), $C_{9-}$ mercaptans, $C_{9-}$ alkanes, cyclohexane, methylcyclopentane, methylcyclohexane, benzene, toluene, ethylbenzene, xylene, mesitylene, $C_{9-}$ alcohols, 2-ethyl-1-hexanol, and the like, or combinations thereof. In an embodiment, the lights fraction can comprise less than about 10 wt. %, alternatively less than about 5 wt. %, alternatively less than about 4 wt. %, alternatively at less than about 3 wt. %, alternatively less than about 2 wt. %, alternatively less than about 1 wt. % $C_{10+}$ compounds, based on the total weight of the lights fraction.

In an embodiment, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins can comprise, can consist essentially of, or can be, a $C_8$ monoolefin (e.g., 1-octene).

In an embodiment, the $C_{9-}$ mercaptans can comprise, can consist essentially of, or can be, a $C_7$ mercaptan, a $C_8$ mercaptan, a $C_9$ mercaptan, or combinations thereof; alternatively, a $C_7$ mercaptan; alternatively, a $C_8$ mercaptan; or alternatively, a $C_9$ mercaptan. In some embodiments, the $C_{9-}$ mercaptans can comprise, can consist essentially of, or can be, a $C_8$ mercaptan.

Following removal of the lights (for example, via flashing), a combined intermediate and heavy fraction (i.e., $C_{10+}$ compounds sometimes referred to as a kettle product) can remain, and the combined intermediate and heavy fraction can be used "as is" or can be further processed, for example separated or split into separate intermediate and heavy fractions (and said separate intermediate and heavy fractions can be subsequently recombined in various blends and associated blend ratios), as described in more detail herein. In an embodiment, a combined intermediate and heavy fraction (i.e., $C_{10+}$ compounds) formed by removal of the lights fraction from the crude composition can comprise less than about 15 wt. %, alternatively less than about 10 wt. %, alternatively less than about 9 wt. %, alternatively less than about 8 wt. %, alternatively less than about 7 wt. %, alternatively less than about 6 wt. %, alternatively less than about 5 wt. %, alternatively less than about 4 wt. %, alternatively less than about 3 wt. %, alternatively less than about 2 wt. %, alternatively less than about 1 wt. % $C_{9-}$ products, based on the total weight of the combined intermediate and heavy fraction (i.e., $C_{10+}$ compounds).

In an embodiment, a combined intermediate and heavy fraction (i.e., $C_{10+}$ compounds) can comprise (A) at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans; wherein at least about 50 wt. %, alternatively at least about 60 wt. %, alternatively at least about 70 wt. %, alternatively at least about 75 wt. %. alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2- mercapto-octane (represented by Structure G), 5-methyl-5-mercapto-nonane (represented by Structure H), and combinations thereof; and (B) at least about 10 wt. %, alternatively at least about 15 wt. %, alternatively at least about 20 wt. %, alternatively at least about 25 wt. % sulfides, or alternatively at least about 30 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction as described herein to produce a combined intermediate and heavy fraction (i.e., $C_{10+}$ compounds) comprising: (A) at least about 25, 30, 35, 40, 45, 50, 55, 60, 65, 70, 75, 80, or 85 wt. % $C_{10}$ branched mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 5 wt. %, alternatively at least about 10 wt. %, alternatively at least about 15 wt. %, alternatively at least about 20 wt. %, alternatively at least about 25 wt. %, or alternatively at least about 30 wt. % branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction as described herein to produce a combined intermediate and heavy fraction (i.e., $C_{10+}$ compounds) comprising: (A) from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) from at least about 10 wt. % to at least about 30 wt. %, alternatively from at least about 10 wt. % to at least about 25 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction and subsequently further separated to produce an intermediate fraction and a heavies fraction. The intermediate fraction and the heavies fractions can then be optionally further processed (e.g., polished) and mixed in any appropriate ratio to produce a blended composition comprising: (A) at least about 25 wt. %, alternatively at least about 30 wt. %, alternatively at least about 40 wt. %, alternatively at least about 50 wt. %, alternatively at least about 80 wt. %, or alternatively at least about 90 wt. % $C_{10}$ mercaptans (e.g., branched $C_{10}$ mercaptans) selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; (B) at least about 5 wt. %, alternatively at least about 10 wt. %, alternatively at least about 15 wt. %, alternatively at least about 20 wt. %, alternatively at least about 25 wt. %, or alternatively at least about 30 wt. % $C_{20}$ sulfides (e.g., branched $C_{20}$ sulfides) represented by structure $R^1$—S—$R^2$, wherein $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof; and one or more of the following components (C)-(I): (C) less than about 5 wt. %, alternatively less than about 4 wt. %, alternatively less than about 3 wt. %, alternatively less than about 2 wt. %, or alternatively less than about 1 wt. % $C_8$ mercaptans; (D) less than about 15 wt. %, alternatively less than about 10 wt. %, or alternatively less than about 5 wt. % $C_{12}$ mercaptans; (E) less than about 15 wt. %, alternatively less than about 10 wt. %, or alternatively less than about 5 wt. % $C_{14}$ mercaptans; (F) less than about 5 wt. %, alternatively less than about 4 wt. %, alternatively less than about 3 wt. %, alternatively less than about 2 wt. %, or alternatively less than about 1 wt. % $C_{16}$ mercaptans and/or $C_{18}$ mercaptans; (G) less than about 1 wt. %, alternatively less than about 0.5 wt. %, alternatively less than about 0.4 wt. %, alternatively less than about 0.3 wt. %, alternatively less than about 0.2 wt. %, or alternatively less than about 0.1 wt. % $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; (H) less than about 10 wt. %, alternatively less than about 5 wt. %, alternatively less than about 4 wt. %, alternatively less than about 3 wt.

%, alternatively less than about 2 wt. %, or alternatively less than about 1 wt. % unreacted $C_{8-18}$ monoolefins; and (I) less than about 10 wt. %, alternatively less than about 5 wt. %, alternatively less than about 4 wt. %, alternatively less than about 3 wt. %, alternatively less than about 2 wt. %, or alternatively less than about 1 wt. % non-olefin impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate. In various embodiments, the blended composition can comprise varying amounts of each of components (C)-(I), and the presence of each component (C)-(I) and the amount thereof can be independently formulated and/or controlled. In various embodiments, the blended composition can comprise an amount of one or more components (C)-(I) that is greater than zero (i.e., above a detection limit associated with the component) and less than the upper range endpoint set forth above (e.g., component (C) is present in the composition in an amount greater than zero and less than about 5 wt. %, and so forth as set forth above).

In some embodiments, a mercaptan/sulfide composition of the type disclosed herein can be prepared by combining at least a portion of a first mercaptan/sulfide composition (wherein only a lights fraction has been removed from the crude product to yield a combined intermediate and heavy fraction, e.g., $C_{10+}$ compounds) with at least a portion of a heavies fraction comprising a sulfide composition to yield a second mercaptan/sulfide composition, wherein a sulfide content of the second mercaptan/sulfide composition is greater than a sulfide content of the first mercaptan/sulfide composition.

In an embodiment, the crude can be separated into light, intermediate, and heavy fractions by distillation, for example in a single distillation column having a light fraction recovered as an overhead stream, an intermediate fraction (e.g., comprising branched $C_{10}$ mercaptans) recovered as a side stream, and a heavy fraction (e.g., comprising branched $C_{20}$ sulfides) recovered as a bottom stream. In alternative embodiments, the separation can be in sequential steps such as removal of the lights fraction in a first distillation column, followed by separation of the intermediate fraction (e.g., comprising branched $C_{10}$ mercaptans) as an overhead stream in a second distillation column and the heavy fraction (e.g., comprising $C_{11+}$ compounds, including branched $C_{20}$ sulfides) as a bottom stream of the second distillation column. These "rough-cut" light, intermediate, and heavy streams can be used "as is" or they can be further processed (e.g., further refined or polished, for example by additional distillation or other separation techniques to produce "fine-cuts") and/or blended to obtain a variety of products that are salable or otherwise available for a variety of end uses such as mining ore collector compositions or chain transfer agents. For example, a variety of mercaptan compositions, sulfide compositions, and mixed mercaptan/sulfide compositions can be produced of the type disclosed in more detail herein.

In an embodiment, an intermediate fraction can comprise at least about 25 wt. %, alternatively at least about 30 wt. %, alternatively at least about 40 wt. %, alternatively at least about 50 wt. % branched $C_{10}$ mercaptans, alternatively at least about 75 wt. % branched $C_{10}$ mercaptans, or alternatively at least about 85 wt. % branched $C_{10}$ mercaptans. In such embodiment, the branched $C_{10}$ mercaptans can be selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In an embodiment, the heavy fraction can comprise at least about 5, 10, 15, 20, 25, 30, 35, 40, 45, 50, 55, 60, 65, 70, 75, 80, or 85 wt. %, branched $C_{20}$ sulfides represented by structure $R^1$—S—$R^2$, wherein both $R^1$ and $R^2$ are each independently a branched $C_{10}$ alkyl group derived from the branched $C_{10}$ monoolefin, and wherein the branched $C_{10}$ alkyl group is selected from the group consisting of

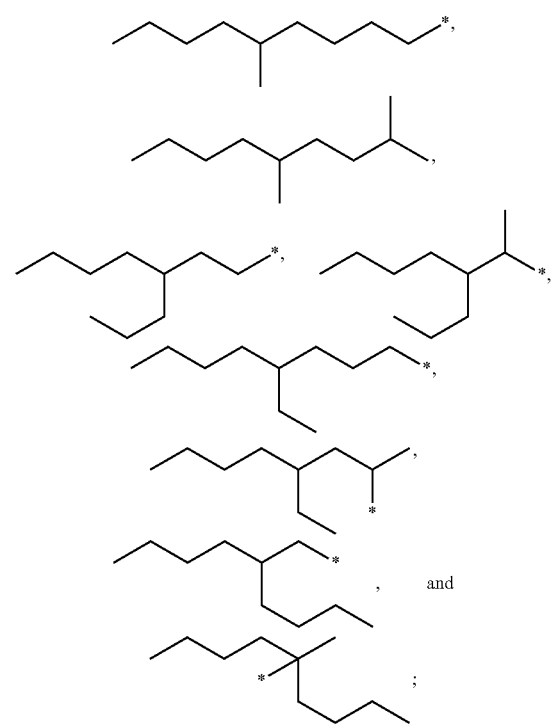

wherein * designates the attachment point to the S atom of the branched $C_{20}$ sulfide.

In an embodiment, a mercaptan composition can comprise mercaptans, wherein at least a portion of the mercaptans comprise $C_{10}$ mercaptans, and wherein at least a portion of the $C_{10}$ mercaptans comprise branched $C_{10}$ mercaptans. In an embodiment, the branched $C_{10}$ mercaptans can comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof.

Structure A

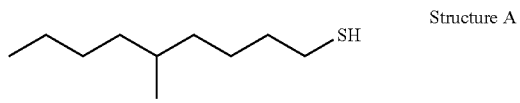

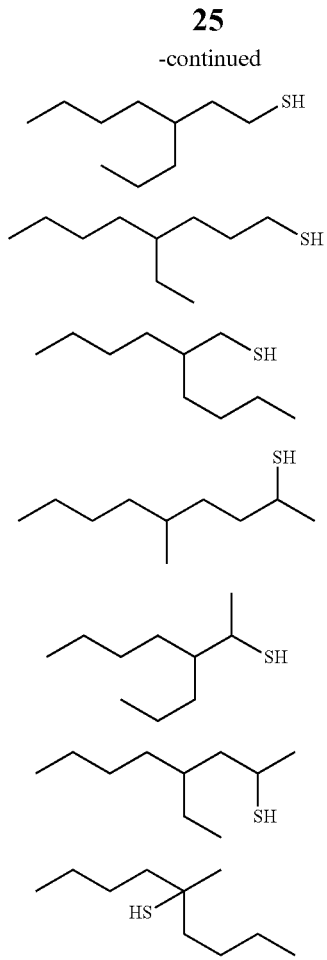

Structure B

Structure C

Structure D

Structure E

Structure F

Structure G

Structure H

For purposes of the disclosure herein, branched $C_{10}$ mercaptans refer to mercaptans (or thiols) that are characterized by the general formula R—SH, wherein R is a branched alkyl group (as opposed to a linear alkyl group), i.e., an alkyl group substituted with alkyl substituents; and wherein R has a total of 10 carbon atoms. Further, for purposes of the disclosure herein, a composition comprising mercaptans, wherein at least a portion of the mercaptans are branched $C_{10}$ mercaptans (e.g., 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof), can also be referred to as a "branched $C_{10}$ mercaptan composition." In an embodiment, the mercaptan composition can comprise any suitable amount of branched $C_{10}$ mercaptans.

In an embodiment, the $C_{10}$ mercaptans can further comprise non-branched $C_{10}$ mercaptans, such as for example 1-mercapto-decane (represented by Structure M), 4-mercapto-decane (represented by Structure N), 5-mercapto-decane (represented by Structure O), 2-mercapto-decane (represented by Structure P), or combinations thereof.

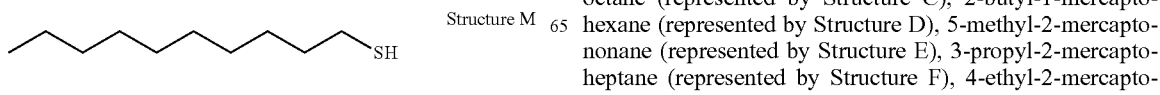

Structure M

Structure N

Structure O

Structure P

In some embodiments, a mercaptan composition can comprise mercaptans, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In other embodiments, a mercaptan composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In yet other embodiments, a mercaptan composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans; wherein at least about 50 wt. %, alternatively at least about 60 wt. %, alternatively at least about 70 wt. %, alternatively at least about 75 wt. %, alternatively at least about 80 wt. %, or alternatively at least 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercaptooctane (represented by Structure G), 5-methyl-5-mercapto-nonane (represented by Structure H), and combinations thereof.

In yet other embodiments, a mercaptan composition can comprise at least about 50, 55, 60, 65, 70, 75, 80, 85, 90, 95, or 99 wt. % mercaptans; wherein at least about 25, 30, 35, 40, 45, 50, 55, 60, 65, 70, 75, 80, 85, 90, 95, or 99 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can comprise from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can consist of or consist essentially of branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can comprise at least about 1, 5, 10, 15, 20, 25, 30, 35, 40, 45, 50, 55, 60, 65, 70, 75, 80, 85, 90, 95, or 99 wt. % branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a composition can comprise mercaptans, wherein at least about 50, 55, 60, 65, 70, 75, 80, 85, 90, 95, or 99 wt. % of the mercaptans are branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In an embodiment, a sulfide composition can comprise sulfides, wherein at least a portion of the sulfides comprise $C_{20}$ sulfides, and wherein at least a portion of the $C_{20}$ sulfides comprise branched $C_{20}$ sulfides represented by structure $R^1$—S—$R^2$, wherein $R^1$ and $R^2$ can each independently be an alkyl group, and wherein at least a portion of the alkyl groups comprises a branched $C_{10}$ alkyl group. In an embodiment, the alkyl group (e.g., a branched $C_{10}$ alkyl group as $R^1$, $R^2$) can comprise a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

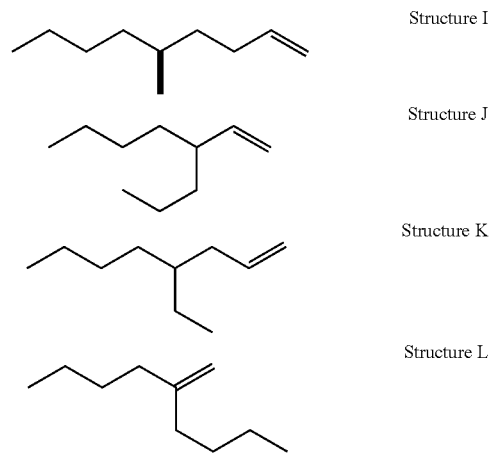

Structure I

Structure J

Structure K

Structure L

For purposes of the disclosure herein a sulfide will be referred to by the total number of carbon atoms (as opposed to the number of carbons of only one of the alkyl groups present in a dialkyl sulfide). For example, a $H_{21}C_{10}$—S—$C_{10}H_{21}$ sulfide will be referred to as a $C_{20}$ sulfide (rather than a $C_{10}$ sulfide). For purposes of the disclosure herein, branched $C_{20}$ sulfides refer to sulfides (or thioethers) that are characterized by the general formula $R^1$—S—$R^2$, wherein both $R^1$ and $R^2$ are each independently a branched $C_{10}$ alkyl group (as opposed to a linear alkyl group), i.e., an alkyl group substituted with alkyl substituents. Stated alternatively, branched $C_{20}$ sulfides refer to sulfides wherein both $R^1$ and $R^2$ are branched $C_{10}$ alkyl groups, wherein $R^1$ and $R^2$ can be the same or different. Further, for purposes of the disclosure herein, a composition comprising sulfides, wherein at least a portion of the sulfides are branched $C_{20}$ sulfides represented by structure $R^1$—S—$R^2$, wherein both $R^1$ and $R^2$ are each independently an alkyl group, wherein at least a portion of the alkyl group comprises a branched $C_{10}$ alkyl group (e.g., a functional group derived from an olefin, and wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof), can also be referred to as a "branched $C_{20}$ sulfide composition." In an embodiment, the sulfide composition can comprise any suitable amount of branched $C_{20}$ sulfides.

In an embodiment, a sulfide composition can comprise sulfides, wherein at least a portion of the sulfides comprise $C_{20}$ sulfides, and wherein at least a portion of the $C_{20}$ sulfides comprise branched $C_{20}$ sulfides represented by structure $R^1$—S—$R^2$, wherein both $R^1$ and $R^2$ can each independently be a branched $C_{10}$ alkyl group derived from a branched $C_{10}$ monoolefin, and wherein the branched $C_{10}$ alkyl group is selected from the group consisting of

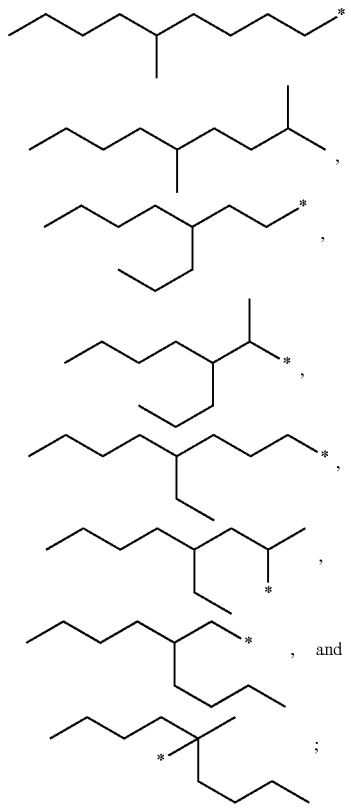

wherein * designates the attachment point to the S atom of the branched $C_{20}$ sulfide. In an embodiment, the branched $C_{10}$ monoolefin can comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof. Generally, a monoolefin is a linear or branched aliphatic hydrocarbon olefin that has one and only one carbon-carbon double bond. Generally, a $C_n$ monoolefin is a linear or branched aliphatic hydrocarbon olefin that has n and only n carbon atoms, and one and only one carbon-carbon double bond. A $C_{10}$ monoolefin is a linear or branched aliphatic hydrocarbon olefin that has ten and only ten carbon atoms, and one and only one carbon-carbon double bond. A branched $C_{10}$ monoolefin is a branched aliphatic hydrocarbon olefin that has ten and only ten carbon atoms, and one and only one carbon-carbon double bond.

In an embodiment, the $C_{20}$ sulfides can further comprise non-branched $C_{20}$ sulfides and/or partially branched $C_{20}$ sulfides represented by structure $R^1$—S—$R^2$, wherein both $R^1$ and $R^2$ (in the case of non-branched $C_{20}$ sulfides) or one of the $R^1$ and $R^2$ (in the case of partially-branched $C_{20}$ sulfides) can be a linear $C_{10}$ alkyl group derived from a linear $C_{10}$ monoolefin, such as for example 4-decene (represented by Structure Q), 5-decene (represented by Structure R), 1-decene (represented by Structure S), or combinations thereof.

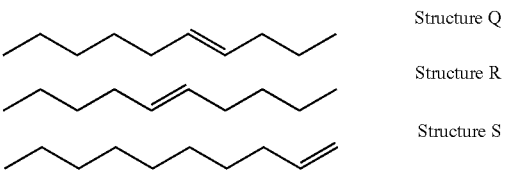

For purposes of the disclosure herein, the non-branched $C_{20}$ sulfides represented by structure $R^1$—S—$R^2$ are the sulfides wherein both $R^1$ and $R^2$ are each independently a linear $C_{10}$ alkyl group derived from a linear $C_{10}$ monoolefin. Further, for purposes of the disclosure herein, the partially branched $C_{20}$ sulfides represented by structure $R^1$—S—$R^2$ are the sulfides wherein one of the $R^1$ and $R^2$ is a linear $C_{10}$ alkyl group derived from a linear $C_{10}$ monoolefin, while the other one of the $R^1$ and $R^2$ is a branched $C_{10}$ alkyl group derived from a branched $C_{10}$ monoolefin as described herein.

In some embodiments, a sulfide composition can comprise sulfides, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In other embodiments, a sulfide composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In other embodiments, a sulfide composition can comprise at least about 1, 5, 10, 15, 20, 25, 30, 35, 40, 45, 50, 55, 60, 65, 70, 75, 80, 85, 90, 95, or 99 wt. %, sulfides, wherein at least about 1, 5, 10, 15, 20, 25, 30, 35, 40, 45, 50, 55, 60, 65, 70, 75, 80, 85, 90, 95, or 99 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In yet other embodiments, a sulfide composition can comprise at least about 10 wt. %, alternatively at least about 15 wt. %, alternatively at least about 20 wt. %, or alternatively at least about 25 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can comprise from at least about 10 wt. % to at least about 30 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can consist of or consist essentially of branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can comprise at least about 5 wt. %, alternatively at least about 10 wt. %, alternatively at least about 15 wt. %, or alternatively at least about 20 wt. % $C_{20}$ sulfides (e.g., branched $C_{20}$ sulfides) represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition comprises at least about 1, 5, 10, 15, 20, 25, 30, 35, 40, 45, 50, 55, 60, 65, 70, 75, 80, 85, 90, 95, or 99 wt. % branched $C_{20}$ sulfides represented by the structure $R^1$—S—$R^2$, wherein $R^1$ and $R^2$ are each independently a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, a mercaptan/sulfide composition can comprise one or more mercaptans and one or more sulfides of the type disclosed herein. For purposes of the disclosure herein, a composition comprising (i) mercaptans, wherein at least a portion of the mercaptans are branched $C_{10}$ mercaptans, and (ii) sulfides, wherein at least a portion of the sulfides are branched $C_{20}$ sulfides, can also be referred to as a "branched $C_{10}$ mercaptan/$C_{20}$ sulfide composition." In an embodiment, the mercaptan/sulfide composition can comprise any suitable amount of branched $C_{10}$ mercaptans, and any suitable amount of branched $C_{20}$ sulfides.

In an embodiment, a mercaptan/sulfide composition can comprise (A) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, a mercaptan/sulfide composition can comprise $C_{10}$ mercaptans represented by the general formula R—SH and/or $C_{20}$ sulfides represented by structure $R^1$—S—$R^2$ that are formed by reacting an olefin feedstock comprising olefins with $H_2S$ as described in more detail herein, wherein the olefins present in the olefin feedstock provide the alkyl group represented by R, $R^1$, and $R^2$. In such embodiments, the R group of the $C_{10}$ mercaptans and/or the $R^1$ and $R^2$ groups of the $C_{20}$ sulfides are provided by or derived from the counterpart R, $R^1$, and $R^2$ groups present in the olefins in the olefin feedstock. In an embodiment, R, $R^1$ and $R^2$ can each independently be an alkyl group, wherein at least a portion of the alkyl groups can comprise a functional group derived from an olefin, wherein the olefin is present in a feedstock (e.g., a first feedstock as described herein) comprising a) at least about 76 mol %, alternatively at least about 78 mol %, alternatively at least about 80 mol %, or alternatively at least about 82 mol % $C_{10}$ monoolefins; and b) at least about 1 mol %, alternatively at least about 2 mol %, alternatively at least about 3 mol %, or alternatively at least about 4 mol % $C_{14}$ monoolefins. In such embodiment, the $C_{10}$ monoolefins can comprise i) at least about 3 mol %, alternatively at least about 4 mol %, alternatively at least about 5 mol %, alternatively at least about 6 mol %, alternatively at least about 7 mol %, or alternatively at least about 8 mol % 2-butyl-1-hexene (represented by Structure L), ii) at least about 8 mol %, alternatively at least about 9 mol %, alternatively at least about 10 mol %, alternatively at least about 11 mol %, alternatively at least about 12 mol %, or alternatively at least about 13 mol % 3-propyl-1-heptene (represented by Structure J), iii) at least about 6 mol %, alternatively at least about 7 mol %, alternatively at least about 8 mol %, alternatively at least about 9 mol %, alternatively at least about 10 mol %, or alternatively at least about 11 mol % 4-ethyl-1-octene (represented by Structure K), and iv) at least about 20 mol %, alternatively at least about 22 mol %, alternatively at least about 24 mol %, alternatively at least about 26 mol %, alternatively at least about 28 mol %, or alternatively at least about 30 mol % 5-methyl-1-nonene (represented by Structure I). In an embodiment, the $C_{10}$ monoolefins can comprise from about 1 mol % to about 16 mol %, alternatively from about 2 mol % to about 15 mol %, alternatively from about 3 mol % to about 14 mol %, alternatively from about 4 mol % to about 13 mol %, or alternatively from about 6 mol % to about 12 mol % 4-decene and/or 5-decene. In an embodiment, the $C_{10}$ monoolefins can comprise from about 0.5 mol % to about 9 mol %, alternatively from about 1 mol % to about 8 mol %, alternatively from about 1.5 mol % to about 7 mol %, or alternatively from about 2 mol % to about 6 mol % 1-decene.

In an embodiment, the olefin (e.g., corresponding to R, $R^1$ or $R^2$) present in the olefin feedstock (e.g., a first feedstock as described herein) can further comprise from about 0.1 mol % to about 5 mol %, alternatively from about 0.25 mol % to about 4 mol %, or alternatively from about 0.5 mol % to about 3 mol % $C_{12}$ monoolefins. In such embodiment, the $C_{12}$ monoolefins can comprise from about 54 mol % to about 74 mol %, alternatively from about 56 mol % to about 72 mol %, alternatively from about 58 mol % to about 70 mol %, or alternatively from about 60 mol % to about 68 mol % 1-dodecene.

In an embodiment, the olefin (e.g., corresponding to R, $R^1$ or $R^2$) present in the olefin feedstock (e.g., a first feedstock as described herein) can further comprise from about 0.1 mol % to about 5 mol %, alternatively from about 0.25 mol % to about 4 mol %, or alternatively from about 0.5 mol % to about 3 mol % $C_8$ monoolefins. In such embodiment, the $C_8$ monoolefins can comprise at least about 95 mol %, alternatively at least about 96 mol %, alternatively at least about 97 mol %, alternatively at least about 98 mol %, or alternatively at least about 99 mol % 1-octene.

In an embodiment, the olefin (e.g., corresponding to R, $R^1$ or $R^2$) present in the olefin feedstock (e.g., a first feedstock as described herein) can further comprise from about 0.05 mol % to about 2 mol %, alternatively from about 0.04 mol % to about 1.5 mol %, alternatively from about 0.06 mol % to about 1.25 mol %, alternatively from about 0.08 mol % to about 1 mol %, or alternatively from about 0.1 mol % to about 0.75 mol % $C_{16}$ monoolefins and/or $C_{18}$ monoolefins.

In an embodiment where the R group of the $C_{10}$ mercaptans and/or the $R^1$ and $R^2$ groups of the $C_{20}$ sulfides are provided by or derived from the counterpart R, $R^1$, and $R^2$ groups present in the olefins in the olefin feedstock (e.g., a first feedstock obtained from a 1-hexene process as described herein), the resultant mercaptan/sulfide composition can be a crude composition that can be further separated and refined into other compositions as described herein.

In an embodiment, mercaptan compositions, sulfide compositions, and/or mercaptan/sulfide compositions as disclosed herein advantageously display improvements in one or more composition characteristics when compared to otherwise similar compositions lacking branched $C_{10}$ mercaptans.

In an embodiment, a mercaptan composition and/or a mercaptan/sulfide composition comprising equal to or greater than about 25 wt. % $C_{10}$ branched mercaptans as disclosed herein can advantageously have an odor less unpleasant and less offensive than an odor of an otherwise similar composition comprising equal to or greater than about 25 wt. % n-decyl mercaptan, as perceived by equal to or greater than about 51% of human subjects exposed to the odor of each composition.

In an embodiment, a mercaptan composition and/or a mercaptan/sulfide composition comprising equal to or greater than about 25 wt. % $C_{10}$ branched mercaptans as disclosed herein can advantageously have an odor less unpleasant than an odor of an otherwise similar composition comprising equal to or greater than about 25 wt. % n-dodecyl mercaptan and/or tert-dodecyl mercaptan, as perceived by equal to or greater than about 51% of human subjects exposed to the odor of each composition. Additional advantages of the mercaptan compositions, sulfide compositions, and/or mercaptan/sulfide compositions and processes of producing same as disclosed herein can be apparent to one of skill in the art viewing this disclosure.

Mining Collector Compositions

Alternative embodiments of the invention also are directed to collector compositions (such as mining chemical collector compositions) for recovering one or more metals from mined ore wherein the collector compositions comprise any of the branched $C_{10}$ mercaptan and/or any of the branched $C_{20}$ sulfide compositions in any of the amounts described herein and above. Unexpectedly, it was found that the branched $C_{10}$ mercaptan and/or branched $C_{20}$ sulfide compositions disclosed hereinabove are very effective at removing metals from mining ores. Moreover, it was unexpectedly found that compositions comprising branched $C_{10}$ mercaptans alone or in combination with the branched $C_{20}$ sulfides do not have an undesirable or offensive odor often associated with other mercaptan mining collectors (e.g., tert-dodecyl mercaptans and n-dodecyl mercaptans).

The branched $C_{10}$ mercaptan and/or branched $C_{20}$ sulfide compositions in the collector composition can collectively be referred to as the "sulfur-containing compounds" of the collector composition.

In various embodiments, the sulfur-containing compounds in the collector composition can be described as mercaptan compositions (e.g., a composition comprising one or more branched $C_{10}$ mercaptans); sulfide compositions (e.g., a composition comprising one or more branched $C_{20}$ sulfides); compositions comprising both mercaptans (e.g., branched $C_{10}$ mercaptans) and sulfides (e.g., branched $C_{20}$ sulfides) and referred to as mercaptan/sulfide compositions; a crude composition (e.g., a crude reaction product as described herein); an intermediate fraction; a heavy fraction; a branched $C_{10}$ mercaptan composition; a branched $C_{20}$ sulfide composition; a branched $C_{10}$ mercaptan/$C_{20}$ sulfide composition; or combinations thereof, as each of these terms is defined, described, and otherwise used herein.

In an embodiment, the sulfur-containing compounds of the mining collector composition can comprise $C_{10}$ mercaptan compounds, wherein at least 50 wt. %, alternatively at least 60 wt. %, alternatively at least 70 wt. %, alternatively at least 80 wt. %, alternatively at least 85 wt. %, alternatively at least 90 wt. %, alternatively at least 95 wt. %, or alternatively at least 99 wt. % of the $C_{10}$ mercaptan compounds are branched, and wherein the branched $C_{10}$ mercaptans are selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In an embodiment, the sulfur-containing compounds of the mining collector compositions can consist essentially of $C_{10}$ mercaptan compounds, wherein the composition comprises (A) at least 85 wt. %, alternatively at least 90 wt. %, alternatively at least 95 wt. %, alternatively at least 99 wt. %, alternatively at least 99.9 wt. % $C_{10}$ mercaptans, and wherein at least 50 wt. % of the $C_{10}$ mercaptans are branched mercaptans as previously described herein. In an alternative embodiment, the mining collector can consist essentially of $C_{10}$ mercaptan compounds wherein a least 50 wt. % of the $C_{10}$ mercaptans are branched mercaptans as previously described herein; (B) less than about 5 wt. %, alternatively less than about 4 wt. %, alternatively less than about 3 wt. %, alternatively less than about 2 wt. %, or alternatively less than about 1 wt. % $C_8$ mercaptans; (C) less than about 15 wt. %, alternatively less than about 10 wt. %, alternatively less than about 5 wt. %, or alternatively less than about 1 wt. % $C_{12}$ mercaptans; (D) less than about 15 wt. %, alternatively less than about 10 wt. %, alternatively less than about 5 wt. %, or alternatively less than about 1 wt. % $C_{14}$ mercaptans; (F) less than about 5 wt. %, alternatively less than about 4 wt. %, alternatively less than about 3 wt. %, alternatively less than about 2 wt. %, or alternatively less than about 1 wt. % $C_{16}$ mercaptans and/or $C_{18}$ mercaptans; (E) less than about 1 wt. %, alternatively less than about 0.5 wt. %, alternatively less than about 0.4 wt. %, alternatively less than about 0.3 wt. %, alternatively less than about 0.2 wt. %, or alternatively less than about 0.1 wt. % $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; (F) less than about 10 wt. %, alternatively less than about 5 wt. %, alternatively less than about 4 wt. %, alternatively less than about 3 wt. %, alternatively less than about 2 wt. %, or alternatively less than about 1 wt. % unreacted $C_{8-18}$ monoolefins; and (G) less than about 10 wt. %, alternatively less than about 5 wt. %, alternatively less than about 4 wt. %, alternatively less than about 3 wt. %, alternatively less than about 2 wt. %, or alternatively less than about 1 wt. % non-olefin components selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate.

In an alternative embodiment, the sulfur containing compounds of the mining collector compositions comprise both $C_{10}$ mercaptans and $C_{20}$ sulfides, wherein (A) at least 50 wt. %, alternatively at least 60 wt. %, alternatively at least 70 wt. %, alternatively at least 80 wt. %, alternatively at least 85 wt. %, alternatively at least 90 wt. %, alternatively at least 95 wt. %, or alternatively at least 99 wt. % of the $C_{10}$ mercaptan compounds are branched, wherein the branched $C_{10}$ mercaptans are selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least 50 wt. %, alternatively at least 60 wt. %, alternatively at least 70 wt. %, alternatively at least 80 wt. %, alternatively at least 85 wt. %, alternatively at least 90 wt. %, alternatively at least 95 wt. %, or alternatively at least 99 wt. % of the $C_{20}$ sulfides are branched $C_{20}$ sulfides of the type and structure as previously described herein.

In an alternative embodiment, the sulfur containing compounds of the mining collector composition comprise both $C_{10}$ mercaptans and $C_{20}$ sulfides, wherein (A) the $C_{20}$ sulfides comprise at least 20 wt. %, alternatively at least 30 wt. %, alternatively at least 40 wt. %, alternatively at least 50 wt. %, alternatively at least 60 wt. %, alternatively at least 70 wt. %, alternatively at least 75 wt. %, or alternatively equal to or less than 80 wt. % of the total composition; (B) the $C_{20}$ sulfides comprise branched $C_{20}$ sulfides of the type and structure as previously described herein; and (C) the total composition comprises less than about 5 wt. %, alternatively less than about 4 wt. %, alternatively less than about 3 wt. %, alternatively less than about 2 wt. %, or alternatively less than about 1 wt. % $C_8$ mercaptans; less than about 10 wt. %, alternatively less than about 5 wt. %, alternatively less than about 4 wt. %, alternatively less than about 3 wt. %, alternatively less than about 2 wt. %, or alternatively less than about 1 wt. % unreacted $C_{8-18}$ monoolefins; and less than about 10 wt. %, alternatively less than about 5 wt. %, alternatively less than about 4 wt. %, alternatively less than about 3 wt. %, alternatively less than about 2 wt. %, or alternatively less than about 1 wt. % non-olefin components selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate.

In a preferred embodiment, the sulfur containing compounds of the mining collector compositions comprise both $C_{10}$ mercaptans and $C_{20}$ sulfides, wherein (A) the $C_{20}$ sulfides comprise between about greater than or equal to 20 wt. % and less than or equal to about 80 wt. % of the total composition; (B) the $C_{20}$ sulfides comprise branched $C_{20}$ sulfides of the type and structure as previously described herein; and (C) the total composition comprises less than about 5 wt. %, alternatively less than about 4 wt. %, alternatively less than about 3 wt. %, alternatively less than about 2 wt. %, or alternatively less than about 1 wt. % $C_8$ mercaptans; less than about 10 wt. %, alternatively less than about 5 wt. %, alternatively less than about 4 wt. %, alternatively less than about 3 wt. %, alternatively less than about 2 wt. %, or alternatively less than about 1 wt. % unreacted $C_{8-18}$ monoolefins; and less than about 10 wt. %, alternatively less than about 5 wt. %, alternatively less than about 4 wt. %, alternatively less than about 3 wt. %, alternatively less than about 2 wt. %, or alternatively less than about 1 wt. % non-olefin components selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate.

While not wishing to be limited by theory, as described in this disclosure and as known by one of ordinary skill in the art, these and other specific compositions can be obtained any number of ways including but not limited to (A) removing $H_2S$ and distilling the light compounds from the crude reaction product or (B) separating the light fraction, the $C_{10}$ mercaptans, the intermediate fraction and the heavy fraction of the crude reaction mixture in any order or by any means to produce two or more partially purified fractions and then blending any two or more of the $C_{10}$ mercaptan fraction, the intermediate fraction, and the heavy fraction to produce the desired composition. For example, the $C_{10}$ mercaptan fraction can be blended with the heavy fraction in various ratios; alternatively, the intermediate fraction, which also comprises the $C_{10}$ mercaptans, can be blended with the heavy fraction in various ratios.

In embodiments, the sulfur-containing compounds of the collector compositions disclosed herein have an odor which is less unpleasant and/or less offensive than an odor of other mercaptan compounds which include n-decyl mercaptans, n-dodecyl mercaptans, tert-dodecyl mercaptans, or combinations thereof present in an amount of equal to or greater than about 25 wt. % of the mercaptan compounds in an otherwise similar mining collector composition.

The amount of the sulfur-containing compounds present in the collector composition can be less than 0.1 wt. %, alternatively less than 0.01 wt. %, or alternatively less than 0.001 wt. % based on the combined total weight of the collector composition and the ore.

The collector composition can further include water, a pH control agent, a frothing agent, a hydrocarbon, an oily reagent, a water immiscible liquid, or combinations thereof.

Nonlimiting examples of water include tap, distilled, well, osmosis, ground, lake, pond, and rain water. The amount of water in the collector composition can be greater than 75 wt. %, greater than 95 wt. %, or greater than 99 wt. %, and typical non-limiting ranges include from 75 to 99.99 wt. %, from 95 to 99.99 wt. %, or from 99 to 99.99 wt. % water, based on the total weight of the collector composition.

Nonlimiting examples of pH control agent include lime, carbonate compounds, the like, or combinations thereof. Suitable amounts of pH control agent in the collector composition include the amounts disclosed in any of the comparative and inventive examples below.

Nonlimiting examples of frothing agents include pine oil; alcohols such as methyl isobutyl carbinol (MIBC); polyether alcohols such as NALFLOTE® 9837 and Cytec OREPREP® X-133; or combinations thereof. Suitable amounts of frothing agent in the collector composition include the amounts disclosed in any of the comparative and inventive examples below.

Moreover, the sulfur-containing compounds disclosed herein can be used alone or in combination with other suitable (second) collector agents in a collector composition. Thus, any of the collector compositions can further comprise a second collector agent, non-limiting examples of which can include a xanthate, a xanthic ester, a thionocarbonate, a dialkyl dithiophosphate, the like, others known in the art with the aid of this disclosure, or combinations thereof. Additionally, the sulfur-containing compounds disclosed herein can be mixed or diluted with other liquids, including but not limited to hydrocarbons and other water immiscible or oily reagents, prior to use in a collector composition.

Also provided herein are flotation processes or procedures for the recovery of metals from ores. The metal can be recovered in any form, for instance, a metal-containing compound (e.g., copper sulfides, molybdenum sulfides), a metal ion, or elemental metal, as well as combinations thereof.

One such flotation process for the recovery of a metal from an ore can comprise contacting the ore with any of the collector compositions disclosed herein (or any of the sulfur-containing compounds disclosed herein). Any suitable order of contacting any components of the collector composition with the ore can be used; and such collector compositions, whether solutions, slurries, blends, immiscible mixtures, and so forth, are encompassed herein. For instance, a ground ore can be contacted with, in any order, the sulfur-containing compounds disclosed herein, a frothing agent, a pH control agent, and a first amount of water (which can be relatively small), resulting in a slurry of the ore and a collector composition comprising the sulfur-containing compounds, the frothing agent, the pH control agent, and water. In some embodiments, a second amount of water (which can be relatively large) can be added to this slurry prior to the flotation process, resulting in a slurry of the ore in a collector composition comprising lower concentrations of the sulfur-containing compounds, the frothing agent, and the pH control agent. In a preferred embodiment, the ore is contacted with the sulfur-containing compounds prior to being mixed with any water, pH control agent, or frothing agent. In yet another preferred embodiment, the ore is contacted with the sulfur-containing compounds prior to forming any slurry. Other suitable methods and orders of forming the collector compositions, whether in the presence of the ore or not, would be readily recognized by those of skill in the art, and such are encompassed herein.

Embodiments of the flotation processes disclosed herein generally include contacting the ore (e.g., ore particles of a desired size) with the sulfur-containing compounds disclosed herein before, during, or after: i) any step of the flotation processes disclosed herein, ii) any step of a specified flotation process, and iii) any step of a flotation process known in the art but not specifically disclosed herein. For example, the sulfur-containing compounds can be contacted with an ore or ore particles of a desired size: i) during grinding of the ore to a desired particle size (and optionally before, after, or with the addition of one or more other components of the collector composition), ii) after grinding (e.g., the sulfur-containing compounds can be added to a flotation cell containing the ore particles, and optionally before, after, or with the addition of one or more other components of the collector composition), iii) during or after adjusting the pH of the material in the flotation cell (e.g., the sulfur-containing compounds can be added to a flotation cell containing the ore particles, and optionally before, after, or with the addition of one or more other components of the collector composition), iv) between and/or during froth removal stages (e.g., the sulfur-containing compounds can be added to the flotation cell, and optionally before, after, or with the addition of one or more other components of the collector composition), v) before, during, or after any other step in a flotation process or procedure disclosed herein, specified by a mine, and/or known in the art, vi) or combinations thereof. It is contemplated that contacting the disclosed sulfur-containing compounds with an ore or ore particles includes a series of additions of the sulfur-containing compounds (alone or in combination with one or more other components of the collector composition) to a rod mill, a flotation cell, or other equipment containing the ore or ore particles.

Equipment and techniques for the flotation recovery of various metals from mining ores are well known to those of skill in the art and are illustrated representatively herein in the examples that follow.

Generally, the metal recovered from the ore comprises a transition metal, one or more Group 3-12 metals. In some embodiments, the metal can comprise a Group 3-11 transition metal, or a Group 5-12 transition metal, while in other embodiments, the metal can comprise gold, silver, platinum, copper, nickel, iron, lead, zinc, molybdenum, cobalt, or chromium, as well as combinations thereof. In particular embodiments of this invention, the metal can comprise copper and molybdenum; alternatively, copper; or alternatively, molybdenum. In addition, other transition metals, such as iron, can be recovered along with copper and/or molybdenum. In embodiments, the metal in the ore is in the form of a metal sulfide. The metal sulfide can comprise copper sulfide, molybdenum sulfide, or combinations thereof.

The flotation processes and collector compositions described herein are not limited to any particular ore. However, the effectiveness of such processes and compositions are particularly beneficial when the ore comprises a copper-bearing ore, a molybdenum-bearing ore, or a copper-bearing and molybdenum-bearing ore. Illustrative and non-limiting examples of such ores include chalcopyrite, chalcocite, molybdenite, and the like.

Any suitable amount of the collector composition and/or the sulfur-containing compounds can be used in the flotation recovery processes or procedures. Often, but not limited thereto, the sulfur-containing compounds and the ore are contacted at a weight ratio in a range of from about 0.45 grams (0.001 lb) of the sulfur-containing compounds per metric ton of ore to about 2200 grams (5 lb) of the sulfur-containing compounds per metric ton of ore. In an alternative embodiment, the sulfur-containing compounds and the ore are contacted at a weight ratio in a range of from about 4.5 grams (0.01 lb) of the sulfur-containing compounds per metric ton of ore to about 450 grams (1 lb) of the sulfur-containing compounds per metric ton of ore. In a preferred embodiment, the sulfur-containing compounds and the ore are contacted at a weight ratio in a range of from about 4.5 grams (0.01 lb) of the sulfur containing compounds per metric ton of ore to about 50 grams (0.1 lb) of the sulfur-containing compounds per metric ton of ore.

Unexpectedly, the sulfur-containing compounds disclosed herein, and any resultant collector compositions containing the sulfur-containing compounds, have high recovery rates of certain transition metals. Recovery is defined as the amount (reported as a weight percentage) of the metal that is recovered after the flotation procedure compared to the amount of metal in the original ore sample. For example, the % recovery of copper in the flotation process can be at least about 75 wt. %, at least about 80 wt. %, at least about 85 wt. %, or at least about 90 wt. %, and often as high as 95 wt. %-98 wt. %. Similarly, the % recovery of molybdenum in the flotation process can be at least about 60 wt. %, at least about 65 wt. %, at least about 80 wt. %, at least about 85 wt. %, or at least about 90 wt. %, and often as high as 92 wt. %-97 wt. %. Grade is defined as the amount (reported as a weight percentage) of a particular metal in the ore concentrate, where the ore concentrate is the product recovered from the flotation procedure.

Furthermore and surprisingly, in some embodiments, the % recovery of copper, the % recovery of molybdenum, or the % recovery of copper and molybdenum of the disclosed sulfur-containing compounds, can be the about the same as or greater than that of a mine standard, under the same flotation conditions. As would be recognized by those of skill in the art, a "mine standard" is the prevailing collector composition currently being used for a given ore and/or desired transition metal. Mine standards are discussed in greater detail in the examples that follow.

Additionally or alternatively, the % recovery of copper, the % recovery of molybdenum, or the % recovery of copper and molybdenum of the disclosed sulfur-containing compounds, can be about the same as or greater than that of a mining collector composition containing TDDM (tertiary dodecyl mercaptan) or NDDM (n-dodecyl mercaptan), under the same flotation conditions. Thus, in some instances, the sulfur-containing compounds disclosed herein are superior to TDDM and/or NDDM.

Additionally or alternatively, the % recovery of copper, the % recovery of molybdenum, or the % recovery of copper and molybdenum of the disclosed sulfur-containing compounds, can be about the same as or greater than that of a mining collector composition using linear (unbranched) n-decyl mercaptans, linear (unbranched) $C_{20}$ sulfides, or both linear (unbranched) n-decyl mercaptans and linear (unbranched) $C_{20}$ sulfides, under the same flotation conditions.

Production of $C_{10}$ Mercaptans and $C_{20}$ Sulfides

Hydrogen sulfide ($H_2S$) and a feedstock comprising branched $C_{10}$ monoolefins were reacted in the presence of various initiating agents: UV radiation, an acid catalyst, and a hydrodesulfurization (HDS) catalyst.

Various feedstocks (e.g., olefin feedstocks) were used for reacting with $H_2S$ to produce mercaptans and/or sulfides. More specifically, $C_{10}$ monoolefin feedstocks obtained from 1-hexene production processes were used as feedstocks for reacting with $H_2S$ to produce mercaptans. Additionally, 1-decene was reacted with $H_2S$ in the presence of a UV initiator to produce a mixture of technical grade n-decyl mercaptan and di-n-decyl sulfide. This composition was used for comparative examples.

Gas chromatography (GC)-mass spectrometry (MS) (GC-MS) and nuclear magnetic resonance (NMR) spectroscopy were used for analyzing the composition of olefin feedstocks obtained from 1-hexene production processes as well as the products of the reaction of the olefin feedstocks with $H_2S$.

The compositions comprising $C_{10}$ monoolefins were analyzed by gas GC-MS using a 15 m×0.25 mm×0.5 µm DB-5 column and/or a 40 m×0.1 mm×0.1 µm DB-1 column to determine component identities, and standard GC using a 60 m×0.32 mm×1 µm DB-1 column to determine the quantity of the components present in the compositions. These compositions are measured in area %, which is substantially similar and analogous to wt. %.

Table 1 provides representative information about the typical composition of such an olefin feedstock obtained from 1-hexene production processes to react with $H_2S$ to produce mercaptans.

TABLE 1

Composition of Olefin Feedstock

| Chemical | GC Area % | | | Normalized % |
|---|---|---|---|---|
| cyclohexane | 2.148 | | | |
| octene | 0.036 | $C_8$ olefins | 1.17 | 1.24 |
| 1-octene | 1.135 | | | |
| octane | 0.146 | octane | 0.15 | 0.16 |
| ethylbenzene | 1.684 | | | |
| 3-propyl-1-heptene | 14.590 | $C_{10}$ olefins | 84.16 | 89.11 |
| decene | 0.164 | | | |
| 4-ethyl-1-octene | 13.134 | | | |
| 5-methyl-1-nonene | 32.144 | | | |
| decene | 0.647 | | | |
| 2-butyl-1-hexene | 9.960 | | | |
| decene | 0.320 | | | |
| 4/5 decene | 9.116 | | | |
| 1-decene | 4.086 | | | |
| decane | 0.360 | decane | 0.36 | 0.38 |
| 2-ethyl-1-hexanol | 1.379 | | | |
| dodecene isomers | 0.448 | $C_{12}$ olefins | 1.29 | 1.37 |
| 1-dodecene | 0.842 | | | |
| dodecane | 0.182 | dodecane | 0.18 | 0.19 |
| tetradecenes | 6.710 | $C_{14}$ olefins | 6.71 | 7.11 |
| tetradecane | 0.198 | tetradecane | 0.2 | 0.21 |

TABLE 1-continued

Composition of Olefin Feedstock

| Chemical | GC Area % | | | Normalized % |
|---|---|---|---|---|
| octadecene | 0.222 | $C_{18}$ olefins | 0.22 | 0.23 |
| 2-ethylhexyl-2-ethylhexanoate | 0.069 | | | |
| Unknowns | 0.281 | | | |
| Total | 100.000 | total olefins | 94.44 | 99.06 |

Normalized to include only octane, decane, dodecane, tetradecane, and $C_8$, $C_{10}$, $C_{12}$, $C_{14}$, and $C_{18}$ olefins As can be seen from Table 1, the total olefin content of this particular olefin feedstock (excluding the compounds that are not products of the 1-hexene process) sample is 94.44 area %, and 84.16 area % of the total feedstock is $C_{10}$ olefin isomers. The $C_{10}$ olefins represent over 89 area % of the total olefin content when the sample is normalized to remove the compounds that are not products of the 1-hexene process. Cyclohexane, ethylbenzene, and 2-ethylhexanol can be present in the olefin feedstock as residual components of the 1-hexene oligomerization process. The structures of $C_{10}$ isomers that can be present in the olefin feedstock are shown in Table 2.

TABLE 2

Structures of Decene Olefins and Mercaptan Reaction Products

| Decene fraction | Olefin | Major UV product | Major Acid Catalyst Product |
|---|---|---|---|
| 5-methyl-1-nonene 32.14% (38.19) | [structure] | [structure with SH] | [structure with SH] |
| 3-propyl-1-heptene 14.59% (17.33) | [structure] | [structure with SH] | [structure with SH] |
| 4-ethyl-1-octene 13.13% (15.60) | [structure] | [structure with SH] | [structure with SH] |
| 2-butyl-1-hexene 9.96% (11.83) | [structure] | [structure with SH] | [structure with SH] |
| 4/5 decene 9.12% (10.83) | [structures] | [structures with SH] | [structures with SH] |
| 1-decene 4.09% (4.86) | [structure] | [structure with SH] | [structure with SH] |

In Table 2, the first column provides the name of the isomer, the GC area % of that component in the feedstock from Table 1, and the normalized amount of the isomer typically found in just the $C_{10}$ fraction of the feedstock. Table 2 also displays the structure of the mercaptans that are produced from the $C_{10}$ olefin isomers. The second column shows the structure of the major $C_{10}$ olefin isomers in the feedstock; the third column displays the structure of the major mercaptan isomers produced by a UV-initiated reaction with $H_2S$; and the fourth column displays the structure of the major mercaptan isomers produced by acid catalysis.

A sample of the olefin feedstock was fractionated (e.g., distilled) and only the $C_{10}$ fraction was isolated in high purity (e.g., a purified feedstock). This product was submitted for $H^1$ and $C^{13}$ NMR. The NMR analysis (in mol %) was consistent with the information provided by GC-MS. The NMR confirmed that about 11 mol % of the total was vinylidene (2 butyl-1-hexene isomer) and about 11 mol % of the total purified feedstock was internal olefins (linear decene isomers). The nomenclature for the various $C_{10}$ isomer products is shown in Table 3.

TABLE 3

Nomenclature for Mercaptan Reaction Products

| $C_{10}$ Olefin | UV-initiated Mercaptans | Acid-catalyzed Mercaptans |
| --- | --- | --- |
| 5-methyl-1-nonene | 5-methyl-1-mercapto-nonane | 5-methyl-2-mercapto-nonane |
| 3-propyl-1-heptene | 3-propyl-1-mercapto-heptane | 3-propyl-2-mercapto-heptane |
| 4-ethyl-1-octene | 4-ethyl-1-mercapto-octane | 4-ethyl-mercapto-octane |
| 2-butyl-1-hexene | 2-butyl-1-mercapto-hexane | 5-mercapto-5-methyl-nonane |
| 4-decene | 4-mercapto-decane<br>5-mercapto-decane | 4-mercapto-decane<br>5-mercapto-decane |
| 5-decene | 4-mercapto-decane<br>5-mercapto-decane | 4-mercapto-decane<br>5-mercapto-decane |
| 1-decene | 1-mercapto-decane | 2-mercapto-decane |

Reaction of $H_2S$ with the olefin feedstock (e.g., a feedstock comprising branched $C_{10}$ monoolefins) by UV initiation (e.g., using UV radiation) yielded mostly primary mercaptans, since the terminal olefin and vinylidene isomers yield predominately the anti-Markovnikov product. The minor components were the secondary mercaptans from the terminal olefin and a tertiary mercaptan from the vinylidene isomer. Typically, UV-initiation of a terminal olefin produced primary mercaptans in 92-96 area % range and secondary mercaptans in 4-8 area % range. The linear internal olefin isomers present in the feedstock primarily produced secondary mercaptan isomers. Thus, for the composition of the feedstock disclosed herein, the distribution of mercaptans (i.e., the distribution within the $C_{10}$ fraction) in the resulting reaction product was predominately primary mercaptans at about 80-90 area %. Secondary mercaptans were present at 10-20 area %, and tertiary mercaptans were present at about 0-3 area %. These ranges were calculated by NMR analysis of the reaction product.

Reaction of $H_2S$ with the olefin feedstock over an acid catalyst (such as Filtrol® 24 or Filtrol® 24X), produced as the major product the Markovnikov product. Thus, the major mercaptan isomers contained secondary mercaptans with some tertiary mercaptan. The relative ratio of mercaptans was estimated at 85-90% secondary mercaptan and 10-15% tertiary mercaptan.

Reaction of $H_2S$ with a feedstock comprising branched $C_{10}$ monoolefins in the presence of a hydrodesulfurization (HDS) catalyst (such as Haldor Topsoe TK-554 or TK-570) produced mercaptans primarily similar in distribution to those produced by acid catalysis, which is the Markovnikov distribution. However, the HDS catalyst also produces a significant amount of the anti-Markovnikov product depending on the conditions used in the reaction step. Thus, under the conditions evaluated for this disclosure, the product produced by the HDS catalyst was a blend of the product produced via acid catalysis with some of the components produced by the UV-initiated reaction.

As will be appreciated by one of skill in the art, and with the help of this disclosure, the actual composition of the reaction product will ultimately depend on a number of factors: the exact composition of the feedstock, the ratio of $H_2S$ to olefin that is used to produce the thiols, the catalytic method used to react the $H_2S$ and olefin (UV vs. acid catalysis vs. HDS catalysis) to produce the product, etc. The final product (e.g., any cuts separated from the crude to form, for example, a commercial product) will also depend on the purification step to remove lights and whether a final product containing both mercaptan and sulfide fractions is desired or just one of the fractions, e.g., a mercaptan fraction or a sulfide fraction, is desired.

$H_2S$ to Olefin Ratio:

The $H_2S$ to olefin molar ratio is an important parameter in determining the amount of mercaptan and sulfide produced during the reaction step. This can be true regardless of the catalytic method employed. Without wishing to be limited by theory and in general, the higher the $H_2S$ to olefin molar ratio, the greater the amount of mercaptans that will be produced compared to the amount of sulfides produced.

A general reaction scheme for addition of $H_2S$ to an olefin is shown in FIG. 1, regardless of catalytic method. For a $C_{10}$ olefin fraction, R, R' and R" can be H or $C_1$-$C_8$ with the total of R+R'+R"=8. For 1-decene, R and R'=H and R"=8 and can be a linear or branched alkyl group. For the major isomers in a $C_{10}$ olefin fraction (e.g., a second feedstock as disclosed herein), 5-methyl-1-nonene: R and R'=H and R"=8, but the alkyl group contains branching at the $3^{rd}$ carbon atom of the $C_8$ fraction.

A sulfide fraction can be produced by further reaction of a mercaptan isomer with an olefin. The generic structures of such sulfides are shown in FIG. 1 and this fraction will consist of a variety of isomers with several possible combinations of sulfide structures depending on whether the sulfide is primary to primary, primary to secondary, primary to tertiary, secondary to secondary, secondary to tertiary, or tertiary to tertiary. The structures are complicated by the fact that on the two portions of the sulfide the R, R' and R" value can be the same or different depending on which mercaptan isomer reacts with which olefin isomer. The total number of carbon atoms of the two portions of the sulfide can also have different values for R+R'+R", although the most dominant combination will be where both sides each have a sum of 8 since the $C_{10}$ fraction predominates in the first feedstock and in the second feedstock.

Reaction Conditions:

Three different reaction methods were used to perform the reaction of $H_2S$ with a feedstock comprising branched $C_{10}$ monoolefins: UV initiation, acid catalysis, and HDS catalysis.

$H_2S$ Removal:

In laboratory experimentation, $H_2S$ was removed using a rotoevaporator apparatus under conditions of reduced pressure. Under these conditions, $H_2S$ was removed without removing significant quantities of light compounds.

Analytical Methods:

The weight percentage of thiol sulfur (wt. % SH) was determined analytically by titration using iodine in water as the titrant and methylene chloride/isopropanol as the solvent system. Such titration can also be done by using a silver nitrate titration method. Total sulfur was measured by X-ray using a model SLFA-20 Horiba sulfur-in-oil analyzer. GC analysis was performed using an Agilent Technologies 7890A GC. A 2 m×0.25 mm×1.0 μm film DB-1 capillary column was used for the separation. Operating conditions were as follows: 70° C. initial temperature, 2 min hold time, 8° C./min ramp rate to 200° C. and then 15° C./min ramp rate to 300° C. and hold for 10 minutes. A 2 ml/min helium flow rate at constant flow conditions was used. A flame ionization detector was used. The injector temperature was set at 275° C. and the detector temperature at 300° C. As described previously, these data from these compositions were reported in area %, which is substantially similar and analogous to wt. %. Olefin conversion was monitored using Raman spectroscopy, with a Kaiser Optical System RXN2 4-channel spectrometer. The peak centered at 1640 cm$^{-1}$ was the vinyl olefin, while the peak centered at about 1670 cm$^{-1}$ was the internal olefin.

Figure 2:
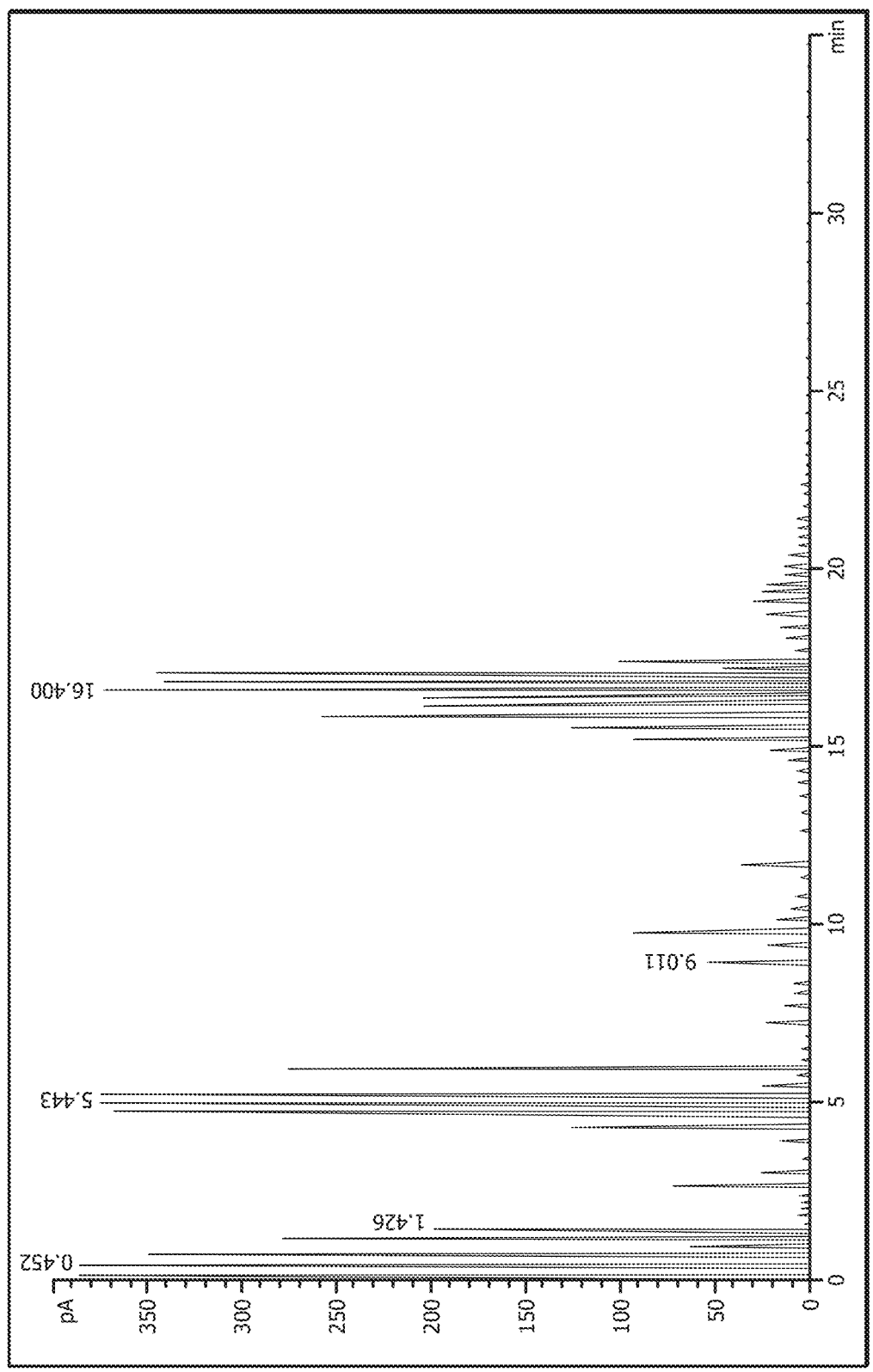
FIG. 2 displays a GC trace of a crude product from an UV initiated reaction after removal of residual $H_2S$.
Figure 4:
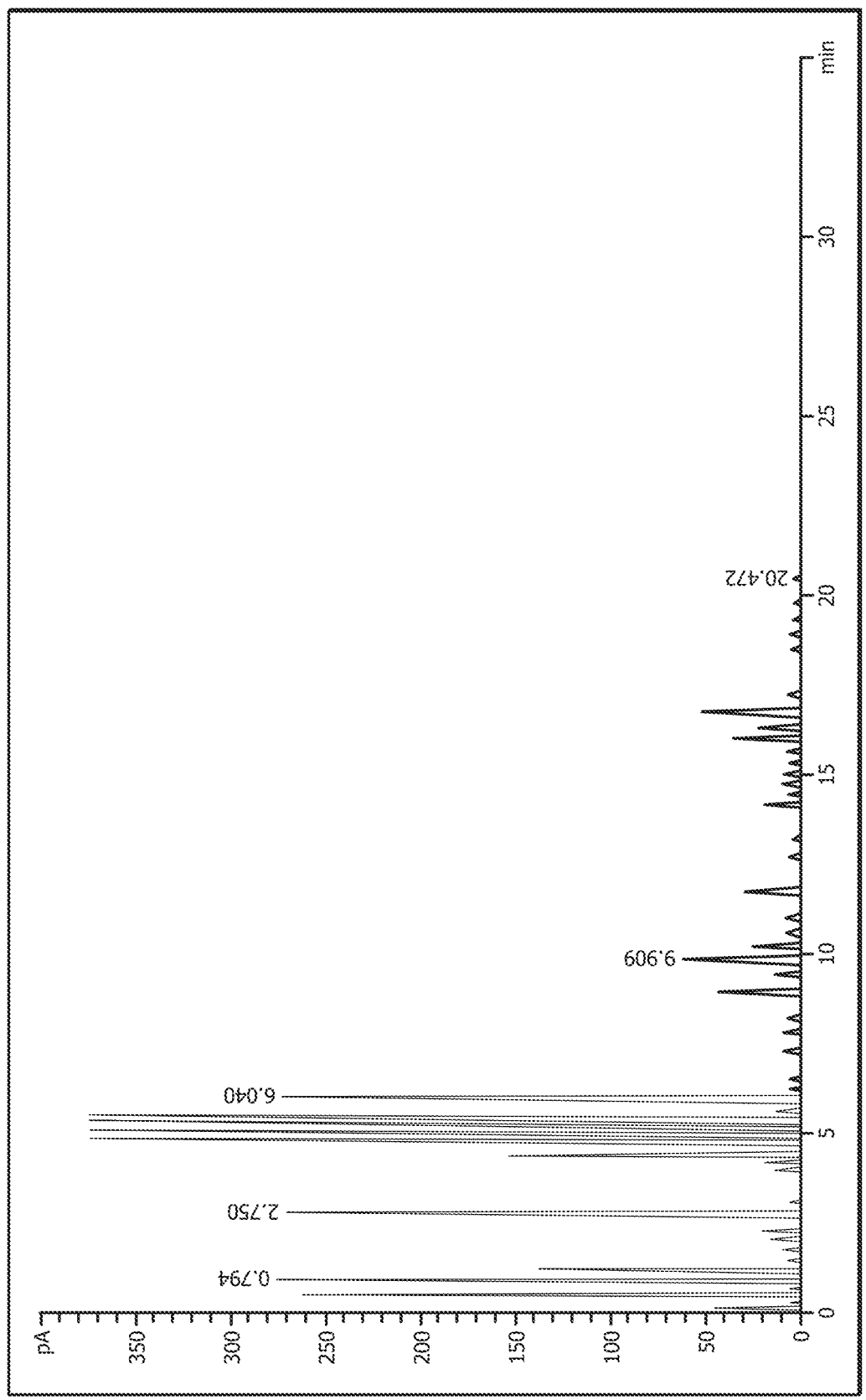
FIG. 4 displays a GC trace of a crude product from an UV initiated reaction after removal of residual $H_2S$.

UV Initiation:

Reactions were performed using either a 1.5 L or a 5-liter UV reactor equipped with a 100 watt lamp and ballast. The two reactors are substantially the same configuration, and the only difference in operation is the amount of reactants added to the reactor. The reaction mixture was stirred at 500-1000 RPM. The reaction temperature was controlled with a bath set at 25° C., but the heat of reaction did reach about 40° C. The lamp operated at 1.1-1.5 amps and 28-103 volts over the course of the reaction, operating at lower amps and higher voltage as it warmed up. The reaction pressure was 220-280 psig (1,516 kPag-1,930 kPag) during the actual reaction time. Experiments were performed using $H_2S$:olefin molar ratios of 1.0 and 10.2. The reaction was completed in about 30 minutes based on the results of Raman Spectroscopy but was allowed to continue for 60 minutes to ensure completion. FIGS. 2 and 4 show typical gas chromatogram results of the UV-initiated crude reaction product, at $H_2S$:olefin mole ratios of 1:1 and 10.2:1, respectively, following removal of the $H_2S$ (but prior to removal of any lights or other fractions).

Surprisingly and unexpectedly, after removing these samples from the reactor and venting off the residual $H_2S$ using a rotoevaporator, the odor of this crude product was good. The limited odor of these compositions was an unexpected result that makes these compositions advantageous for use as mining collectors Samples 1, 2, 3, and 4 were all prepared from crude reaction products resulting from the UV-initiation process described in the preceding paragraphs.

Figure 7:
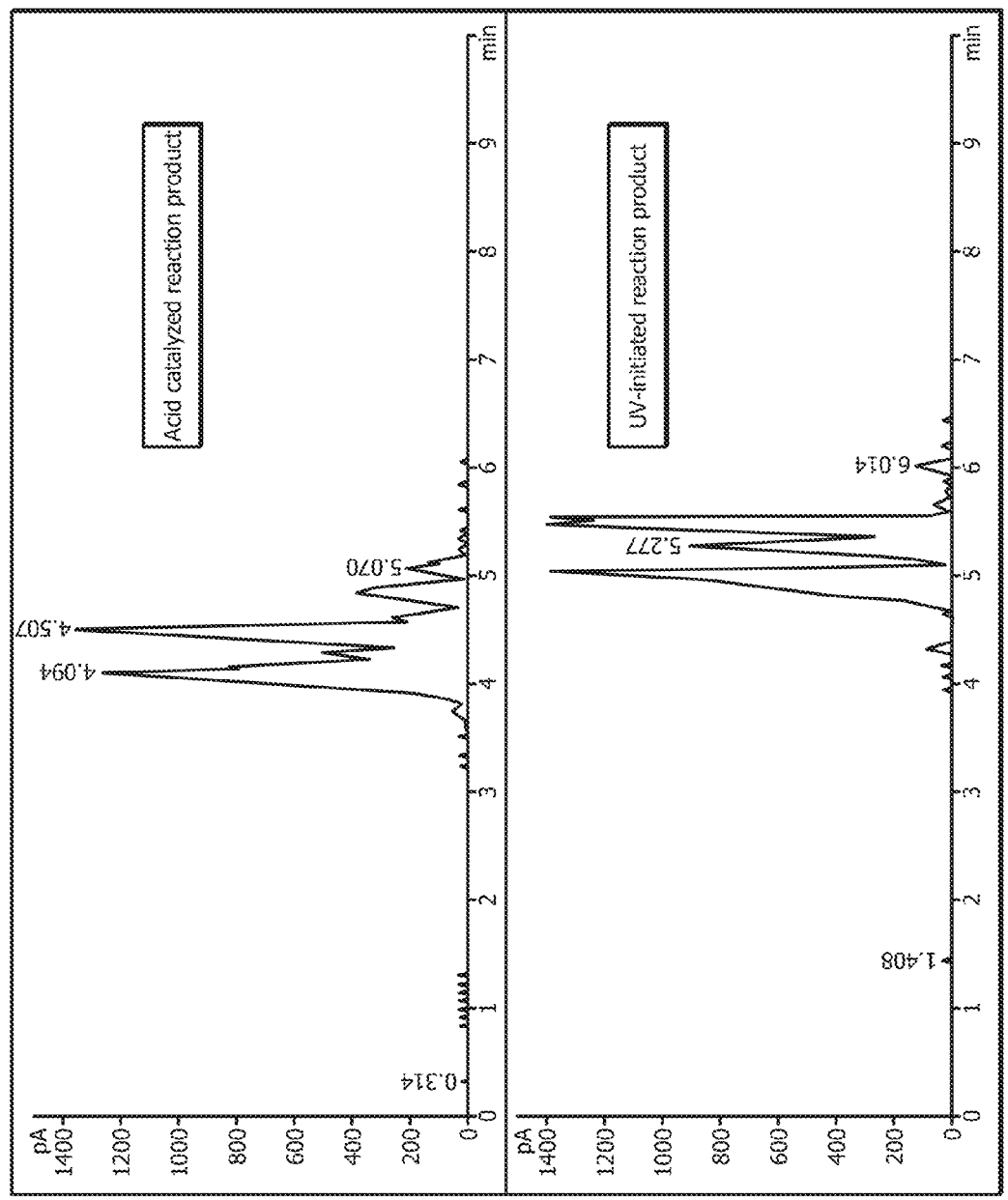
FIG. 7 displays a comparison of GC traces for a $C_{10}$ mercaptan fraction isolated from a product obtained by UV initiation and a $C_{10}$ mercaptan fraction isolated from a product obtained by acid catalysis, and particularly, representative GC profiles of the purified $C_{10}$ mercaptan reaction product. The upper chromatogram is the acid catalyzed $C_{10}$ mercaptan product, and the lower chromatogram is the UV-initiated $C_{10}$ mercaptan product.

Sample 1 (a comparative example) contained primarily $C_{10}$ n-decyl mercaptans, low amounts of linear $C_{20}$ sulfides, and no branched compounds. Sample 1 was prepared from the crude reaction product resulting from the reaction of 1-decene with $H_2S$ via the UV-initiated reaction by distilling the crude product to remove $H_2S$ and any light fractions that were produced. Sample 2 contained mostly $C_{10}$ mercaptans (including branched $C_{10}$ mercaptans as described previously herein), prepared by first removing $H_2S$ and the light fraction, and then distilling the $C_{10}$ mercaptan fraction from the remaining intermediate and heavy crude reaction products to product a high purity $C_{10}$ mercaptan fraction. FIG. 7 shows a typical gas chromatogram analysis of the purified $C_{10}$ mercaptan fraction obtained from the UV-initiated reaction product.

Figure 3:
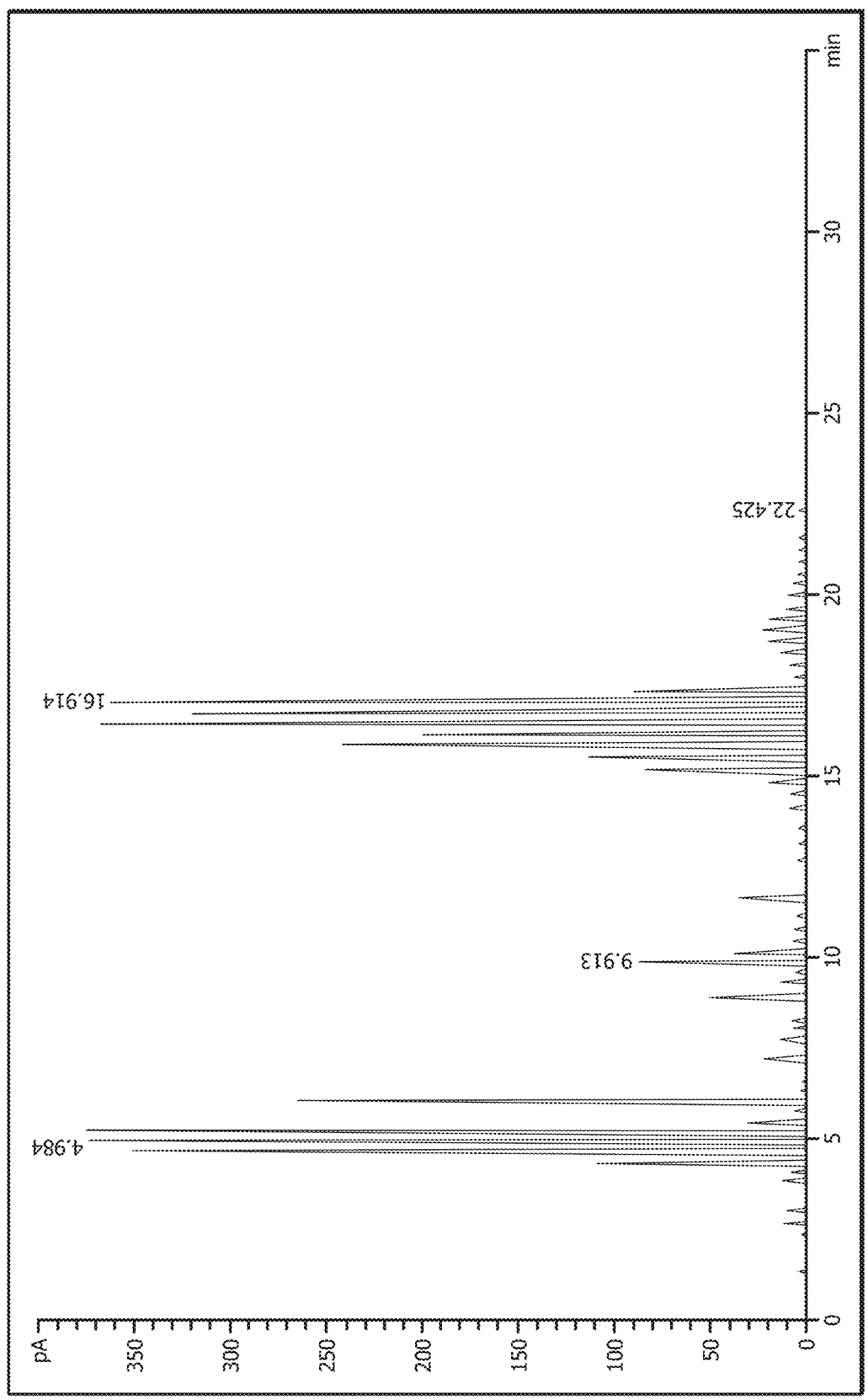
FIG. 3 displays a GC trace of a reaction product from an UV initiated reaction after removal of lights.
Figure 5:
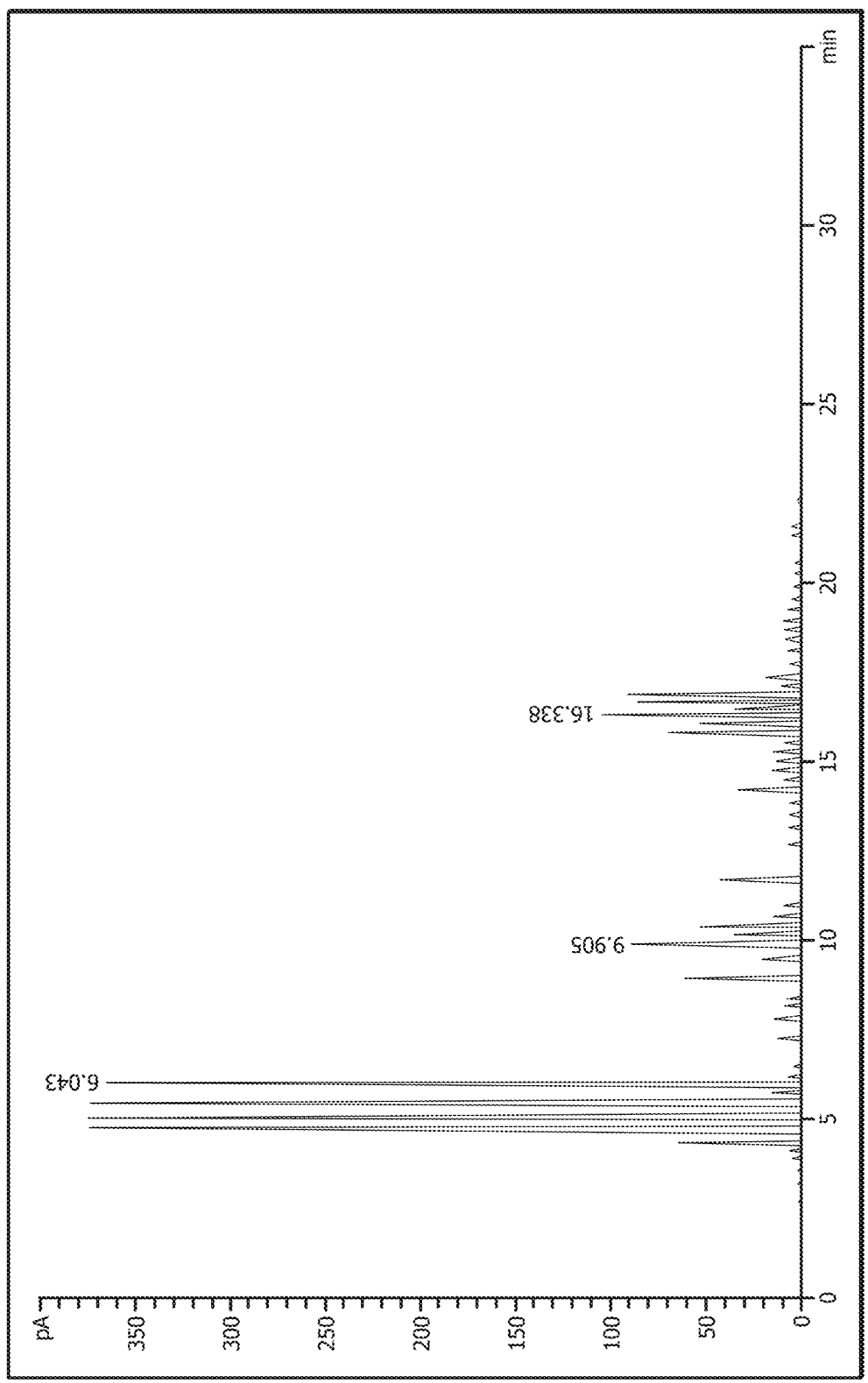
FIG. 5 displays a GC trace of a reaction product from an UV initiated reaction after removal of lights.

Sample 3 contained mostly $C_{20}$ sulfide compounds (including branched $C_{20}$ sulfides as described previously herein) that were left behind after the $H_2S$, lights, and intermediates/mercaptans were distilled from the crude reaction product. Sample 4 contained mixed $C_{10}$ mercaptans and $C_{20}$ sulfides (including branched $C_{10}$ mercaptans and branched $C_{20}$ sulfides as described previously herein), prepared by distilling the crude reaction product to remove $H_2S$ and the light fraction, which included (but is not limited to) cyclohexane, ethylbenzene, 2-ethylhexanol and residual octene, some decene isomers, and the majority of the octylmercaptan. FIGS. 3 and 5 show typical gas chromatogram results of the $C_{10}$ mercaptan/$C_{20}$ sulfide reaction product obtained via the UV-initiated reaction process and following the removal of the light fraction. The distillation process proceeded as follows: The first 7 fractions removed from the crude reaction product were considered to be the light fractions. This distillation step was considered to be complete when the kettle temperature increased from 100° C. to 121° C. and the head temperature increased from room temperature to 98.9° C. Cuts 8-13 were considered to be the intermediate fractions and included the $C_{10}$ mercaptans. These cuts were collected at a kettle temperature of 122° C. to 154° C. and a head temperature of 99° C. to 105° C. Cuts 14 and 15 were collected at kettle and head temperatures of from 122° C. to 154° C. and 103.4° C. to 107.2° C., respectively. These cuts and whatever remained in the kettle were considered the heavies. The head temperature was allowed to increase from room temperature to 107.2° C. before the distillation was stopped. For a typical distillation, only the light fraction was distilled and the reaction product was what remained in the kettle after the lights were removed.

Acid Catalysis:

Acid catalyzed reactions produced a different distribution of isomer products than obtained by UV-initiation reaction of $H_2S$ and the olefin feedstock comprising branched $C_{10}$ monoolefins.

The product produced via the acid catalyzed addition of $H_2S$ to the feedstock comprising branched $C_{10}$ monoolefins was prepared in a continuous flow reactor over Filtrol® 24 acid catalyst. The reactor contained 43.22 g of catalyst and the WHSV (weight hourly space velocity) was maintained at 1.0 grams of olefin per gram of catalyst per hour. The $H_2S$ to olefin molar ratio ranged from 10:1 to 1:1. The reaction temperature was between 120° C. to 220° C., and the reactor pressure was 450-460 psig (3,100 kPa-3,200 kPa).

Acid catalysis produced the Markovnikov product. The vinyl components of the feedstock comprising branched $C_{10}$ monoolefins produced secondary mercaptans. The internal olefin components produced secondary mercaptans, while the vinylidene components produced tertiary mercaptans. Thus, the composition of the $C_{10}$ mercaptan fraction isomers was different when compared to the composition of the product obtained by UV-initiation. For example, the 5-methyl-1-nonene isomer produced 5-methyl-2-mercaptononane via acid catalysis; and 5-methyl-1-mercapto-nonane was the major product produced via UV-initiation, with a minor amount of the 2-mercapto isomer as a by-product. The 2-butyl-1-hexene isomer produced 5-methyl-5-mercaptononane via acid catalysis; while UV-initiation produced 2-butyl-1-mercapto-hexane.

As with the product produced via UV-initiation, the product obtained by acid catalysis consisted of three general fractions after removal of the unwanted lights fraction. The $C_{10}$ mercaptan fraction comprised from 50-100 wt. % of the crude kettle composition. The mercaptan functionality of the $C_{10}$ fraction was 85-95% secondary mercaptan and the remainder tertiary mercaptan. These isomers eluted in the 3.1-6.5 minute range under the utilized GC conditions.

The intermediate fraction consisted of those mercaptan peaks in the 6.5-14 minute range. However, the functionality of the mercaptans was secondary and tertiary $C_{12}$ to $C_{18}$ mercaptans. The intermediate fraction comprised 5-15% of the total kettle composition.

The sulfide fraction comprised 0-70% of the composition of the kettle product. The fraction consisted of sulfides primarily of formula $C_{10}H_{21}$—S—$C_{10}H_{21}$. However, the isomer identity was different than that for the product produced via UV-initiation. The acid produced sulfide product was based on secondary and tertiary mercaptans rather than predominately primary mercaptans as in the UV-initiated produced product.

As with the samples produced via the UV-initiated process, the acid-catalyzed reaction products were subsequently further processed to remove $H_2S$ and distill the crude reaction product into various fractions.

Figure 6:
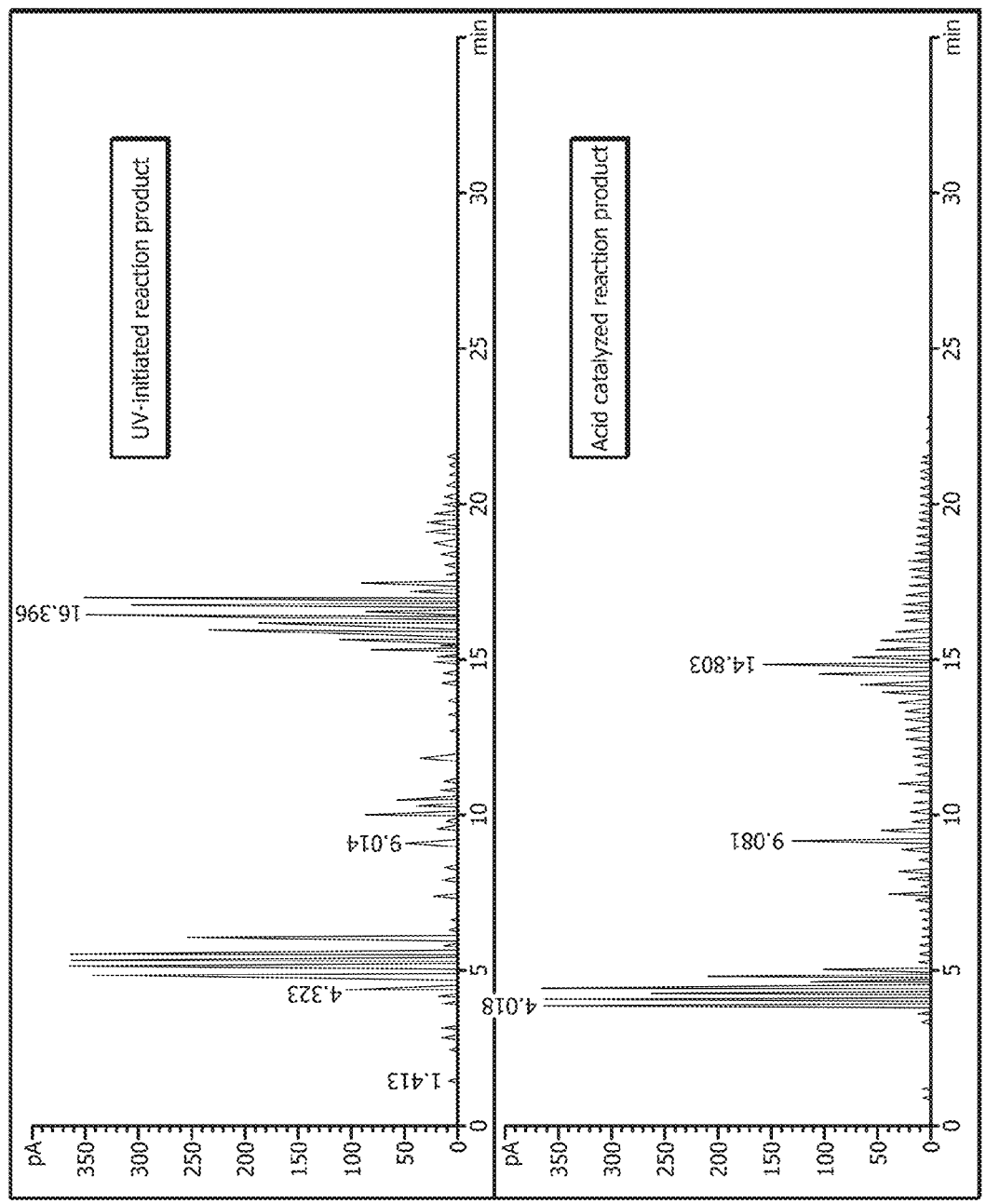
FIG. 6 displays a comparison of GC traces for a product obtained by UV initiation and a product obtained by acid catalysis. The upper chromatogram is the UV-initiated $C_{10}$ mercaptan product, and the lower chromatogram is the acid catalyzed $C_{10}$ mercaptan product.

Samples 5 and 6 were prepared from crude reaction product obtained via acid catalysis. Sample 5 contained primarily mixed $C_{10}$ mercaptans and $C_{20}$ sulfides (including branched $C_{10}$ mercaptans and branched $C_{20}$ sulfides as described previously herein), prepared by distilling the crude reaction product as previously described to remove $H_2S$ and light fractions which included (but are not limited to) cyclohexane, ethylbenzene, 2-ethylhexanol and residual octene, some decene isomers, and the majority of the octylmercaptan. Sample 6 contained primarily $C_{20}$ sulfide compounds (including branched $C_{20}$ sulfides as described previously herein) that were left behind after the $H_2S$, lights, and intermediates/mercaptans, were distilled from the crude reaction product. FIG. 6 shows a typical gas chromatogram analysis of the $C_{10}$ mercaptan/$C_{20}$ sulfide reaction product obtained via acid catalysis process and following the removal of the light fraction.

HDS Catalysis:

Reactions utilizing HDS catalysis produced mercaptans that were primarily similar in distribution to those produced by acid catalysis, which is the Markovnikov distribution. However, there was a tendency to also produce some of the anti-Markovnikov distribution depending on the specific conditions utilized in the reaction step. Thus the product produced by the HDS catalyst appeared to be a blend of product produced primarily via acid catalysis with some of the components of the UV-initiated reaction.

The HDS reaction conditions were as follows: WHSV was varied from 0.75 to 2 grams of olefin per gram of catalyst per hour; the molar ratio of $H_2S$ per olefin was varied from 2:1 to 10:1; the average reaction temperature was 180° C. to 220° C. The catalyst used was cobalt molybdenum on alumina, examples being to Haldor Topsoe TK-554, TK-570, or similar. Olefin conversion, as determined by Raman Spectroscopy, was in the 88-97 mol % range.

Figure 8:
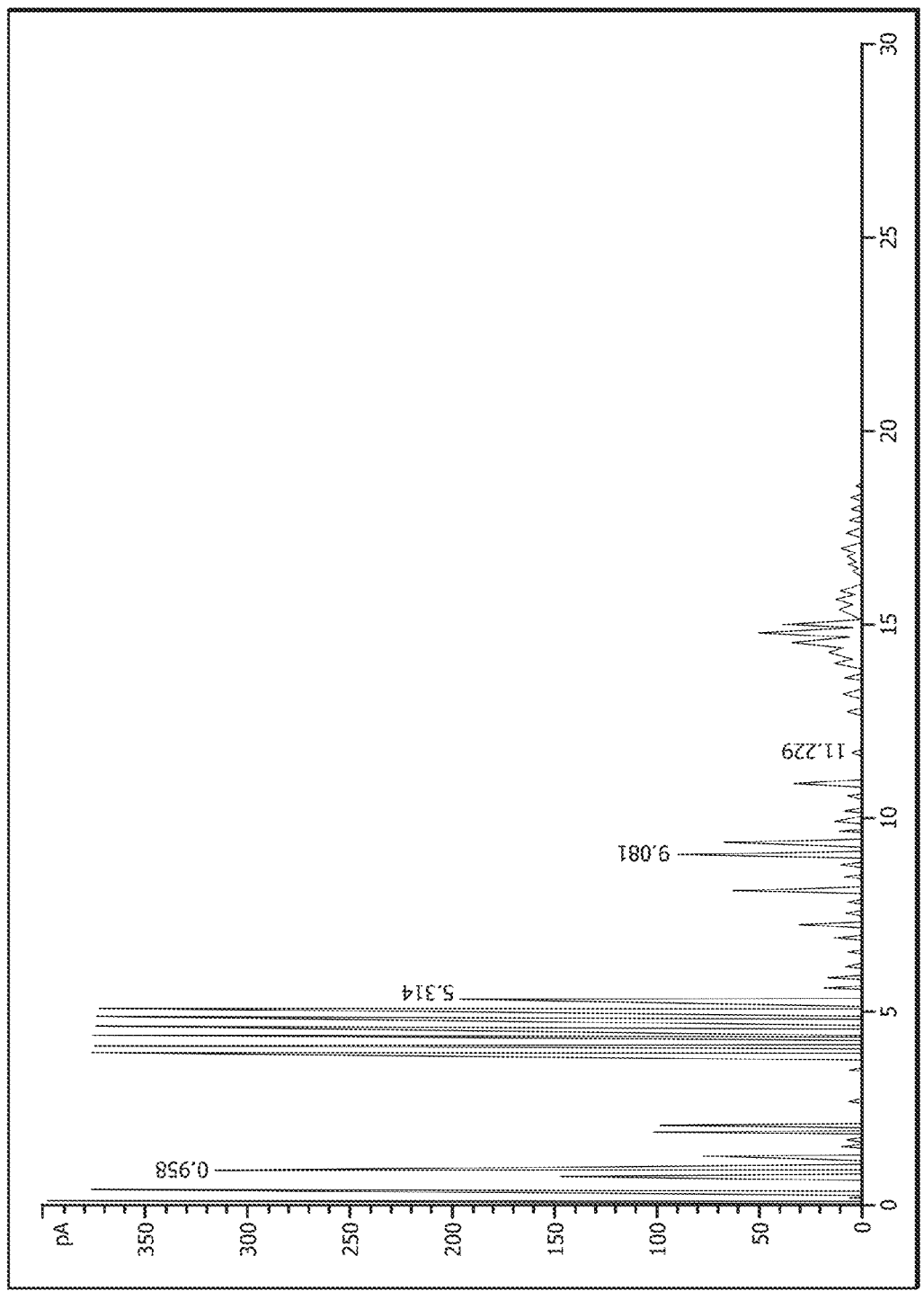
FIG. 8 displays a GC trace of a crude product from a reaction catalyzed by a hydrodesulfurization catalyst after removal of residual $H_2S$.

Under similar conditions of WHSV, ratio and temperature, the HDS catalyzed reaction produced more $C_{10}$ mercaptan fraction and less sulfide fraction than the acid catalyzed reaction. Comparison of the GC analysis of the crude reaction product produced from the HDS catalyzed reaction of $H_2S$ and branched $C_{10}$ monoolefins showed that the HDS-catalyzed reaction produced a crude reaction product that was a blend of the product compositions produced by the UV-initiated and acid-catalyzed reactions. FIG. 8 shows a typical gas chromatogram analysis of the crude reaction product (with only $H_2S$ removed) resulting from the HDS catalyzed reaction.

Recovery of Metals Using the Disclosed Sulfur-Containing Compounds in Collector Compositions The recovery of metals using compositions comprising one or more of the branched $C_{10}$ mercaptans and/or branched $C_{20}$ sulfides of the type described as a collector composition was evaluated. The following examples include comparative examples which use mine standards for the recovery of metals, comparative examples which use Sample 1, and inventive examples which use Samples 2 to 6.

Four ore samples were obtained from four different mines, i.e., Ore 1 from Mine 1, Ore 2 from Mine 2, Ore 3 from Mine 3, and Ore 4 from Mine 4. These ore samples contained metal sulfide minerals from which the metal(s) (e.g., copper and/or molybdenum) can be recovered using collector compositions. Ore 1 can be characterized as containing chalcocite, chalcopyrite, and molybdenite minerals. Ore 2 can be characterized as containing predominantly chalcocite and chalcopyrite minerals. Ore 3 can be characterized as containing chalcocite, chalcopyrite, and molybdenite minerals; however, is different in composition and from a different mine than Ore 1. Ore 4 can be characterized as containing predominantly chalcocite and chalcopyrite minerals; however, is different in composition and from a different mine than Ore 2.

The headgrade of each of the ores is summarized in Table 4 below.

TABLE 4

| Ore Headgrade Summary | | | | | |
|---|---|---|---|---|---|
| Ore | Cu | Fe | Mo | S | Total Insolubles |
| 1 | 0.26 | 2.99 | 0.039 | 0.98 | 82.7 |
| 2 | 0.48 | 2.70 | 0.010 | 0.97 | 90.5 |
| 3 | 0.34 | 2.28 | 0.024 | 1.03 | 91.5 |
| 4 | 0.42 | 2.28 | 0.009 | 1.59 | 77.7 |

Values are shown in wt. % based on the total weight of the ore for copper, iron, molybdenum, sulfur, and total insolubles. Samples were analyzed for molybdenum content by digesting an ore sample over heat in a solution containing potassium chlorate, nitric acid, and hydrochloric acid. After the digested sample was cooled, super floc was added, and the sample was analyzed via atomic absorption using a nitrous oxide-acetylene red flame. Standards ranged from 50-100 ppm by weight molybdenum. A similar procedure with the necessary modifications was used to analyze for copper and iron content.

Determination of Desired or Optimum Grind Time

Each of the metal recovery (e.g., flotation) procedures specified for each of Ore 1, Ore 2, Ore 3, and Ore 4 required grinding the ore to provide the ore samples at a specified particle size. The desired particle size was 30 wt. %+100 mesh solids (meaning 30% of the particles are 149 microns or larger) for Ore 1; 25 wt. %+70 mesh solids (meaning 25% of the particles are larger than 210 microns) for Ore 2; 36 wt. %+100 mesh solids (meaning 36% of the particles are 149 microns or larger) for Ore 3; and 20 wt. %+100 mesh solids (meaning 20% of the particles are 149 microns or larger) for Ore 4. The term "+100" refers to all particles collected on the 100 mesh screen and larger (e.g., 25, 40, etc.). The term "+70" refers to all particles collected on the 70 mesh screen and larger.

To determine the amount of time needed to provide the ores at the specified particle size, referred to as the "desired grind time" or "optimum grind time," an appropriate amount of ore from the appropriate mine (e.g., 900 to 1,000 grams, depending on the ore) was provided at the −10 mesh size. This ore was placed in a rod mill with 20 lb of rods with prescribed sizes (e.g., prescribed by the respective mine), and an appropriate amount of water (e.g., lime water) was added to give the desired solids content. The rod mill was turned on for an amount of time based on prior knowledge of that respective ore or an educated guess based on experience with similar ore materials. After grinding for the desired amount of time, the grind mixture was poured and rinsed with a minimum amount of tap water into a container. The water and solids were poured through a 230 mesh wet screen sieve shaker while washing with water to remove any fines. This was done in two batches to facilitate the washing procedure. Failure to remove the fines often results in the material being glued together in chunks, analogous to concrete. The remaining solids were removed from the screen with washing onto filter paper in a Buchner funnel with vacuum. The solids collected were dried in an oven overnight at 75° C. The dried solids were then screened through a series of screens (25 mesh, 40, 50, 70, 100, 140, 200, 230, and Pan) on a Ro-Tap® shaker in two batches, six minutes each. The above grind procedure was conducted at least three times to give a graph of time vs. wt. % dry solids on a certain mesh screen size.

From the linear plot of this data, the "desired grind time" was determined by adding the amount of solids on the screens up to the desired mesh size for each ore. This procedure can be done periodically, but is necessary if the ore composition or the rod charge changes.

The desired grind time for Ore 1 was about 12 minutes, 18 seconds; the desired grind time for Ore 2 was about 9 minutes, 0 seconds; the desired grind time for Ore 3 was about 5 minutes, 7 seconds; and the desired grind time for Ore 4 was about 13 minutes, 45 seconds.

Flotation Procedure for Ore 1 Using a Mine Standard as Example

The standard flotation procedure for Ore 1 is as follows. A 1-kg charge of Ore 1 was added to a rod mill along with 650 mL tap water and approximately 1 g of lime (this amount can be adjusted to obtain the desired alkalinity, see above). The flotation collector reagents were added to the pool of water (not directly on the solids) in the mill using micro syringes: PAX (potassium amyl xanthate), 0.01 lb/metric ton @ 1% solution (1000 μL), made fresh daily; medium cycle oil (MCO), 0.05 lb/metric ton, 24.6 μL; MC 37 collector (mixture of TDDM and MCO), 0.05 lb/metric ton (26.1 μL); and plant frother (80% Nalco NALFLOTE® 9837/20% Cytec OREPREP® X-133), 28 μL. The mill was placed on rubber rollers and ground for the predetermined time of 12 minutes, 18 seconds. The mill was removed from the rollers and the solids washed into a transparent plastic flotation cell (2.5 L). Only enough water was used to reach the flotation volume (2-liter mark on flotation cell). If too little water was used to wash the material into the flotation cell, additional lime water was added to reach the 2-liter flotation volume. The solids amount was about 32 wt. % for Ore 1. The material was conditioned for two min at 1,200 rpm, then floated for five min at 1,200 rpm. Air was bubbled into solution at the rate of 8 L/min. Froth was removed from the surface of the cell approximately every 10 sec with a plastic paddle. The froth was collected in a glass pan under the lip of the cell. Liquid was added periodically to keep the solution near the lip of the cell so froth could be easily removed. Care was taken to not have froth flow over the lip without raking with the paddle. The standpipe and back cell corners were washed down as needed with lime water. Depending on the frothiness of the ore, it can be necessary to restrict the air at the beginning of the flotation to prevent froth from overflowing the cell on its own. Generally, the air valve was completely open by the end of the first minute. If not, then the amount of frother was adjusted. If it was difficult to maintain complete surface coverage with froth, a few more microliters of frothing agent were added. To do this, the air and timer were shut off, and the froth concentrate was added and conditioned for 30 seconds before turning back on the air and timer.

The air and stirring were turned off and the apparatus washed to remove solids from the stirrer and shaft into the flotation cell. After allowing the solids to settle for a few minutes, a sample was taken for titration to determine alkalinity. The remaining tails were filtered through an 8-inch stainless steel filter (3 gallons) onto shark skin filter paper. The collected solids were dried in an oven at 85° C. overnight to give dry solids that were weighed and labeled as tailings.

The rougher froth concentrate collected in the pan was filtered by washing onto filter paper and dried in an oven at 85° C. overnight. Temperature was kept at/below 85° C. to prevent oxidation and weight changes from occurring. The dried solids were weighed and labeled as concentrate. Both the tailings and concentrate were analyzed for determination of copper, molybdenum, and iron.

The alkalinity titration procedure defined an alkalinity of 1.0 as being equivalent to 0.01 lb of CaO per metric ton of solution. To prepare lime water of 30 alkalinity, 19 g of CaO were added to 50 L of water, agitated for at least one hour, then solids were settled overnight. The lime water was decanted for use. For titration, to a 50 mL alkaline solution, one drop of phenolphthalein indicator solution was added, and titrated with 0.02N $H_2SO_4$ solution until the pink color disappeared. Each mL of titrating solution equaled 2.0 alkalinity units.

Assuming a solution is 30 alkalinity, that is, 0.3 lb CaO per metric ton of solution, then, (0.3 lb CaO/metric ton solution)*(metric ton/2000 lb)*(8.345 lb/gal)*(gal/3.785 L)*(453.6 g/lb) converts to 0.15 g CaO/L, or 0.0075 g CaO/50 mL.

If the molecular weight of CaO=56 g/mol, and the molecular weight of $H_2SO_4$=98 g/mol, and N=Molarity*net positive charge, then $$0.02N\ H_2SO_4=(0.02/2)*(98\ g/mol)=(0.98\ g/L)*(1\ L/1000\ mL)=0.00098\ g/mL.$$

According to the stoichiometry of the reaction:

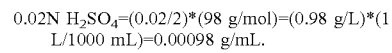

then 98 g $H_2SO_4$ neutralizes 56 g CaO.

If 0.0075 g CaO are present, then 0.0075×98/56=0.013125 gm $H_2SO_4$ are required, and 0.013125 g $H_2SO_4$/0.00098 g/mL=13.393 mL $H_2SO_4$.

Flotation Procedure for Ore 2 Using Mine Standard as Example

The standard flotation procedure for Ore 2 is as follows. The grind size was determined as described hereinabove. The optimum grind time was 9 minutes. One kg bag of ore was charged and 650 mL of water was added to the rod mill. The flotation procedure was carried out as described for the Ore 1, except a time of 9 minutes was used. The standard collector system for this ore was added to the grind: 14 µL of Cytec AERO® MX 7021 and 12.5 µL of Cytec AERO® XD 5002—both of which are modified thionocarbamates. The frother added in the flotation cell was Cytec OREPREP® X-133 at 5.6 µL dosage. The pH was adjusted to 11 with lime and the mixer was started at 1,200 rpm for 1 min during the conditioning phase. The air was started and the froth was scraped for 6 min into one pan. The air was turned off and the final pH was checked. The concentrate and tailings materials were filtered, dried and weighed as described for the Ore 1 procedure.

Flotation Procedure for Ore 3 Using a Mine Standard as Example

The standard flotation procedure for Ore 3 is as follows. The grind size was determined as described hereinabove. The optimum grind time was 5 minutes, 7 seconds. A 900-g charge of ore, 0.6 g of lime, 32.5 µL of diesel, and 600 mL of water were charged into the rod mill. The optimum grind time was utilized and the material transferred to the flotation cell as described above in the Ore 1 procedure. Then, 1,091 µL of a 1% solution of sodium ethyl xanthate and 28 µL of the 80/20 frother mentioned in the Ore 1 procedure were charged to the stirring liquid and conditioned for one min. The froth was collected for 3 min into a collection pan. The air was stopped and another 28 µL of frother and 546 µL of 1% sodium ethyl xanthate were added to the slurry. The air was restarted and a 1-min conditioning phase was performed. The froth was then collected for another 2 min into the collection. The concentrate and tailings material were filtered, dried and weighed as described for the Ore 1 procedure.

Flotation Procedure for Ore 4 Using a Mine Standard as Example

The standard flotation procedure for Ore 4 is as follows. The grind size was determined as described hereinabove, except the desired grind for Ore 4 was 20% plus 100 mesh (meaning 20% of the particles are 149 microns or larger). The optimum grind time to achieve these results was 13.75 minutes. A 1-kg charge of ore was utilized. The amount of lime added to the grind was 1.2 g along with 500 µL of the PAX/Dithiophosphate (DTP) 238 solution. The PAX/DTP 238 solution was prepared by mixing 153 mL of distilled water with 0.5 mL DTP 238 and 0.5 gram of PAX. The pH of the slurry was 10.5 after diluting with 650 mL of water and transferring to the flotation cell and diluting with water up to the 2-L mark. The slurry was stirred without air and 2000 µL of PAX/DTP 238 solution were added along with 34 µL of a 50/50 vol. mixture of pine oil/MIBC. The pulp was stirred at 1,200 rpm for one min and then the 8 L/min air was turned on. The froth was then raked over the weir for 3 min into a pan. The air was turned off and an additional 34 µL of pine oil/MIBC (frother) and 2000 µL of PAX/DTP were added followed by conditioning for 1 min. The air was then turned back on and the froth collected for an additional 3 min into the pan. The air was then turned off while adding another 34 µL of pine oil/MIBC and 2,000 µL of PAX/DTP followed by conditioning for 1 min while stirring. The air was then turned on for another min, followed by collecting the froth for 3 min. The air and stirring were then turned off and the concentrate pan was removed and the pulp mixture vacuum filtered to give the concentrate that was then dried in an oven overnight at 85° C. The tailings mixture was then poured out into a filter with filter paper to obtain a wet tailings mixture. This mixture was dried in an oven overnight at 85° C. The weight of the concentrate and tailings were recorded before analytical analysis.

The mine standards for comparative examples C1 to C4 are shown in Table 5 below:

TABLE 5

Summary of Mine Standards tested for Metals Recovery via Ore Flotation

| Examples | Mine Standard |
|---|---|
| C1 | lime, PAX, MCO, MC 37, and frother |
| C2 | lime, thionocarbamate, and frother |
| C3 | lime, sodium ethyl xanthate solution, diesel, and frother |
| C4 | lime, PAX/DTP 238, and frother |

The flotation procedures above were used for Examples C1 to C4, with the recovery data shown below.

The mine standard for Ore 1 (per metric ton basis) contained 1200 g of lime, 1000 µL of 1% potassium amyl xanthate (PAX), 25 µL of medium cycle oil (MCO), 26 µL of MC 37 (mixture of TDDM and MCO), and 28 µL of plant frother 80% Nalco NALFLOTE® 9837/20% Cytec OREPREP® X-133.

The mine standard for Ore 2 (per metric ton basis) contained 600 g of lime, 12.5 µL of thionocarbamate Cytec AERO® XD 5002, 14 µL of thionocarbamate MX 7021, and 20 µL of frother Cytec AERO® X-133.

The mine standard for Ore 3 (per metric ton basis) contained 600 g of lime, 1637 µL of a 1% sodium ethyl xanthate solution in water, 32.5 µL of diesel, and 56 µL of pine oil/MIBC (frother).

The mine standard for Ore 4 (per metric ton basis) contained 1100 g of lime, 6500 µL of 1% PAX/DTP 238, and 102 µL of pine oil/MIBC (frother).

The flotation procedures above were performed for Comparative Examples C5 to C8 similarly to Comparative Examples C1 to C4. Comparative Examples C5 to C8 substituted the sulfur-containing compounds of Sample 1 for the respective combinations of PAX, MCO, MC 37, thionocarbamate, sodium ethyl xanthate solution, diesel, and PAX/DTP 238 contained in the mine standards of C1 to C4.

Comparative Example C5 for Ore 1 used a collector composition containing 1200 g of lime, Sample 1 in the amount specified in Table 8 below, and 28 µL of plant frother 80% Nalco NALFLOTE® 9837/20% Cytec OREPREP® X-133.

Comparative Example C6 for Ore 2 used a collector composition containing 600 g of lime, Sample 1 in the amount specified in Table 8 below, and 20 µL of Cytec OREPREP® X-133 (frother).

Comparative Example C7 for Ore 3 used a collector composition containing 600 g of lime, Sample 1 in the amount specified in Table 8 below, and 56 µL of pine oil/MIBC (frother).

Comparative Example C8 for Ore 4 used a collector composition containing 1100 g of lime, Sample 1 in the amount specified in Table 8 below, and 102 µL of pine oil/MIBC (frother).

The sulfur-containing compounds used (i.e., Samples 2 to 6) in the collector compositions for the inventive examples are shown in Table 6 below:

TABLE 6

Summary of Sulfur-Containing Compounds Used in the Collector Compositions Tested for Metals Recovery via Ore Flotation

| Examples | Sulfur-Containing Compounds in the Collector Composition | Method of Preparation of the Sulfur-Containing Compounds |
|---|---|---|
| 1 to 4 | Sample 2: $C_{10}$ mercaptans | UV-initiated catalysis of olefin feedstock |
| 5 to 8 | Sample 3: $C_{20}$ sulfides | UV-initiated catalysis of olefin feedstock |
| 9 to 12 | Sample 4: mixed $C_{10}$ mercaptans-$C_{20}$ sulfides | UV-initiated catalysis of olefin feedstock |
| 13 to 16 | Sample 5: mixed $C_{10}$ mercaptans-$C_{20}$ sulfides | Acid catalysis of olefin feedstock |
| 17 to 20 | Sample 6: $C_{20}$ sulfides | Acid catalysis of olefin feedstock |

The flotation procedures above were performed for Examples 1 to 20 similarly to Comparative Examples C1 to C4. Examples 1 to 20 substituted sulfur-containing compounds comprising one of Samples 2 to 6 for the respective combination of PAX, MCO, MC 37, thionocarbamate, sodium ethyl xanthate solution, diesel, and PAX/DTP 238 contained in the mine standards of C1 to C4.

Examples 1, 5, 9, 13, and 17 for Ore 1 used a collector composition containing 1200 g of lime, one of Samples 2 to 6 in the amount specified in the Tables 7-13 below, and 28 µL of plant frother 80% Nalco NALFLOTE® 9837/20% Cytec OREPREP® X-133.

Examples 2, 6, 10, 14, and 18 for Ore 2 used a collector composition containing 600 g of lime, one of Samples 2 to 6 in the amount specified in Tables 7-13 below, and 20 µL of Cytec OREPREP® X-133 (frother).

Examples 3, 7, 11, 15, and 19 for Ore 3 used a collector composition containing 600 g of lime, one of Samples 2 to 6 in the amount specified in Tables 7-13 below, and 56 µL of pine oil/MIBC (frother).

Examples 4, 8, 12, 16, and 20 for Ore 4 used a collector composition containing 1100 g of lime, one of Samples 2 to 6 in the amount specified in Tables 7-13 below, and 102 µL of pine oil/MIBC (frother).

Tables 7 to 13 present data for Comparative Examples C1 to C8 and Examples 1 to 20 regarding the wt. % recoveries of copper, molybdenum, and iron from the four ores tested, using the standard chemical collectors for each ore, comparative sulfur-containing compounds of Sample 1, and the various mercaptan/sulfide compositions of Samples 2 to 6, at different amounts. Duplicates of each flotation experiment were conducted, and the average reported.

TABLE 7

Metals Recovery Using Mine Standards

| Comparative Example | Ore | Recoveries % | | | Grade % | |
|---|---|---|---|---|---|---|
| | | Cu | Mo | Fe | Cu | Mo |
| C1 | 1 | 91.2 | 92.8 | 24.4 | 9.7 | 1.37 |
| C2 | 2 | 88.8 | 72.1 | 33.3 | 9.3 | 0.14 |
| C3 | 3 | 92.8 | 93.7 | 38.7 | 4.8 | 0.34 |
| C4 | 4 | 89.9 | 67.3 | 48.9 | 3.5 | 0.06 |

TABLE 8

Metals Recovery Using a $C_{10}$ n-Decyl Mercaptan-$C_{20}$ Sulfide Composition Produced via UV Catalysis of 1-Decene

| Comparative Example | Ore | Sulfur-Containing Compounds | Recoveries % | | | Grade % | | Dosage |
|---|---|---|---|---|---|---|---|---|
| | | | Cu | Mo | Fe | Cu | Mo | |
| C5 | 1 | Sample 1 | 91.1 | 93.0 | 12.5 | 9.7 | 1.48 | 15 µL |
| C6 | 2 | Sample 1 | 85.7 | 68.2 | 27.9 | 7.1 | 0.12 | 25 µL |
| C7 | 3 | Sample 1 | 94.2 | 95.9 | 35.6 | 7.6 | 0.45 | 15 µL |
| C8 | 4 | Sample 1 | 84.5 | 72.4 | 31.1 | 5.1 | .07 | 15 µL |

TABLE 9

Metals Recovery Using a $C_{10}$ Mercaptan Composition Produced via UV Catalysis of the Olefin Feedstock

| Example | Ore | Sulfur-Containing Compounds | Recoveries % | | | Grade % | | Dosage |
|---|---|---|---|---|---|---|---|---|
| | | | Cu | Mo | Fe | Cu | Mo | |
| 1 | 1 | Sample 2 | 91.1 | 87.0 | 13.1 | 8.7 | 1.42 | 15 uL |
| 2 | 2 | Sample 2 | 83.1 | 73.1 | 24.2 | 8.2 | 0.14 | 15 uL |
| 3 | 3 | Sample 2 | 93.8 | 95.9 | 36.9 | 6.9 | 0.49 | 15 uL |
| 4 | 4 | Sample 2 | 85.2 | 66.5 | 28.4 | 5.6 | 0.09 | 15 uL |

TABLE 10

Metals Recovery Using a $C_{20}$ Sulfide Composition Produced via UV Catalysis of the Olefin Feedstock

| Example | Ore | Sulfur-Containing Compounds | Recoveries % | | | Grade % | | Dosage |
|---|---|---|---|---|---|---|---|---|
| | | | Cu | Mo | Fe | Cu | Mo | |
| 5 | 1 | Sample 3 | 91.8 | 94.8 | 11.7 | 10.5 | 1.62 | 15 µL |
| 6 | 2 | Sample 3 | 68.5 | 57.8 | 20.0 | 8.0 | 0.16 | 25 µL |
| 7 | 3 | Sample 3 | 93.6 | 97.4 | 35.9 | 6.9 | 0.53 | 25 µL |
| 8 | 4 | Sample 3 | 84.9 | 70.1 | 26.1 | 5.3 | 0.10 | 15 µL |

TABLE 11

Metals Recovery Using a Mixed $C_{10}$ Mercaptan-$C_{20}$ Sulfide Composition Produced via UV Catalysis of the Olefin Feedstock

| Example | Ore | Sulfur-Containing Compounds | Recoveries % | | | Grade % | | Dosage |
|---|---|---|---|---|---|---|---|---|
| | | | Cu | Mo | Fe | Cu | Mo | |
| 9 | 1 | Sample 4 | 91.2 | 97.0 | 14.3 | 8.13 | 1.46 | 25 µL |
| 10 | 2 | Sample 4 | 82.1 | 68.5 | 25.9 | 8.59 | 0.14 | 25 µL |
| 11 | 3 | Sample 4 | 95.0 | 98.4 | 38.5 | 7.3 | 0.61 | 15 µL |
| 12 | 4 | Sample 4 | 85.0 | 78.9 | 26.0 | 6.22 | 0.07 | 9 µL |

TABLE 12

Metals Recovery Using a Mixed $C_{10}$ Mercaptan-$C_{20}$ Sulfide Composition Produced via Acid Catalysis of the Olefin Feedstock

| Example | Ore | Sulfur-Containing Compounds | Recoveries % | | | Grade % | | Dosage |
|---|---|---|---|---|---|---|---|---|
| | | | Cu | Mo | Fe | Cu | Mo | |
| 13 | 1 | Sample 5 | 92.4 | 95.1 | 14.5 | 8.35 | 1.14 | 15 μL |
| 14 | 2 | Sample 5 | 85.1 | 66.9 | 30.5 | 8.2 | 0.14 | 25 μL |
| 15 | 3 | Sample 5 | 93.9 | 98.4 | 40.0 | 6.1 | 0.43 | 25 μL |
| 16 | 4 | Sample 5 | 82.7 | 61.8 | 40.6 | 5.25 | 0.10 | 25 μL |

TABLE 13

Metals Recovery Using a $C_{20}$ Sulfide Composition Produced via Acid Catalysis of the Olefin Feedstock

| Example | Ore | Sulfur-Containing Compounds | Recoveries % | | | Grade % | | Dosage |
|---|---|---|---|---|---|---|---|---|
| | | | Cu | Mo | Fe | Cu | Mo | |
| 17 | 1 | Sample 6 | 91.7 | 92.9 | 12.5 | 9.6 | 1.41 | 25 μL |
| 18 | 2 | Sample 6 | 69.9 | 71.3 | 21.3 | 8.2 | 0.17 | 25 μL |
| 19 | 3 | Sample 6 | 94.4 | 96.1 | 37.2 | 6.5 | 0.49 | 15 μL |
| 20 | 4 | Sample 6 | 83.9 | 68.7 | 26.5 | 5.3 | 0.10 | 15 μL |

As shown in Tables 7 to 13, and unexpectedly, the collector compositions used in Examples 1 to 4 and 9 to 16 (containing mercaptan compositions disclosed herein) exhibited % recoveries of molybdenum of at least 60%, and in some cases, greater than 90%. In particular, the collector compositions described herein are capable of improving the molybdenum recovery compared to that achieved using mine standards. As shown in Tables 7-13, all of the compositions derived from the reaction of the olefin feedstock with $H_2S$ resulted in the improved recovery of molybdenum from Ore 3 when used in a collector composition. Unexpectedly, molybdenum recovery ranged from 95.9% up to 98% with these compositions, compared to only 93.7% with the mine standards. Molybdenum recovery was also improved compared to that achieved with the n-decyl mercaptan composition that was produced via the UV-initiated reaction of $H_2S$ with 1-decene. Copper and iron recovery were comparable to that achieved with the standard ore collectors.

Ore 1 also exhibited better molybdenum recoveries using all but one of the compositions derived from the olefin feedstock (87% to 97%) as compared to both the mine standard collector (92.8%) and the n-decyl mercaptan composition (93%). The recovery of copper from Ore 1 was comparable to that of the mine standard. Similarly, specific compositions (including the mixed $C_{10}$ mercaptans/$C_{20}$ sulfides produced via UV initiation and the $C_{20}$ sulfides produced via UV initiation) improved the molybdenum recovery from Ore 4. Ore 2 did not exhibit improved recovery of molybdenum with any of the compositions; however, it is not unexpected for the compositions to perform differently due to the variability in the characteristics of these particular ores.

While not wishing to be limited by theory, the improvement in metal recoveries observed, particularly in Ore 3, are hypothesized to be the result of two possible effects. First, the level of branching in these products is greater than the corresponding n-decyl product in Sample 1. The n-decyl product did not perform as well as the mixed $C_{10}$ mercaptans/$C_{20}$ sulfides composition (Samples 4 and 5) in terms of copper recovery (n-decyl 94.2% vs 95.0%) or molybdenum recovery (n-decyl 95.9% vs 98.4%). Secondly, comparison of the recoveries of the $C_{10}$ mercaptan composition (Sample 2) with the mixed $C_{10}$ mercaptans/$C_{20}$ sulfides composition (Samples 4 and 5) which contains the sulfide heavies, demonstrates better recoveries of copper (95.0% vs. 93.8%) and molybdenum (98.4% vs 95.9%) using the product containing the sulfide heavies. This suggests that both the branched compounds and sulfide heavies are responsible for the improved recovery/grade numbers. It is also interesting to compare the $C_{20}$ sulfide composition (Sample 3, which contained 76.4% $C_{20}$) with that of the $C_{10}$ mercaptans/$C_{20}$ sulfides composition (Sample 4, which contained only 5.1% $C_{20}$ heavies). Note that the copper (95.0% vs. 93.6%) and molybdenum (98.4% vs. 97.4%) recoveries suffered very little by such a dramatic increase in sulfide heavies. Two conclusions can be drawn from these results. First, the sulfide heavy fraction is important to the activity of the reagent, as a more powerful reagent is obtained by leaving the sulfide heavies in the product. The second conclusion is that the level of sulfide heavies can be dramatically increased above what is typically produced in the crude (unpurified or undistilled) reaction mixture.

None of the compositions produced via the reaction of the olefin feedstock with $H_2S$ in the presence of the HDS catalyst were tested in the metal recovery ("flotation") procedures. However, because the composition of the crude reaction product produced using the HDS catalyst is essentially a blend of the compositions produced using a UV-initiator and an acid catalyst, it is expected that compositions derived from the crude reaction product from the HDS-catalyzed reaction would produce very similar results and trends to those observed for the crude reaction products of UV-initiated and acid-catalyzed reactions. In particular, it is expected that Ores 1 and 3 would yield comparable or improved recovery of molybdenum and copper if treated with either a mixed $C_{10}$ mercaptan/$C_{20}$ sulfide composition, a $C_{10}$ mercaptan composition, or a $C_{20}$ sulfide composition produced via HDS catalysis, and Ore 4 would yield comparable recoveries of molybdenum if treated with a mixed $C_{10}$ mercaptan/$C_{20}$ sulfide composition obtained via HDS catalysis.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

Embodiment 1 is a process for the recovery of a metal from an ore. The process comprises contacting the ore with a collector composition, wherein the collector composition comprises sulfur-containing compounds, wherein the sulfur-containing compounds comprise: (i) mercaptans comprising branched $C_{10}$ mercaptans compounds selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (ii)

sulfides comprising branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

Embodiment 2 is the process of embodiment 1, wherein the step of contacting is performed at least once during a metal flotation procedure.

Embodiment 3 is the process of any of embodiments 1 to 2, wherein the sulfur-containing compounds are present in an amount of less than 0.1 wt. % based on a combined total weight of the collector composition and the ore.

Embodiment 4 is the process of any of embodiments 1 to 3, wherein sulfur-containing compounds comprise from about 15 wt. % sulfides to about 80 wt. % sulfides, and wherein the sulfides are the branched $C_{20}$ sulfides.

Embodiment 5 is the process of any of embodiments 1 to 4, wherein the collector composition further comprises water, a pH control agent, a frothing agent, a hydrocarbon, an oily reagent, a water immiscible liquid, or combinations thereof.

Embodiment 6 is the process of any of embodiments 1 to 5, wherein the branched $C_{10}$ mercaptans are present in an amount of at least about 50 wt. % based on a total weight of the mercaptans in the collector composition.

Embodiment 7 is the process of any of embodiments 1 to 6, wherein the branched $C_{20}$ sulfides are present in an amount of at least 50 wt. % based on a total weight of the sulfides in the collector composition.

Embodiment 8 is the process of any of embodiments 1 to 7, wherein the metal comprises gold, silver, platinum, copper, nickel, iron, lead, zinc, molybdenum, cobalt, chromium, or combinations thereof.

Embodiment 9 is the process of any of embodiments 1 to 8, wherein the metal comprises copper, and a percent recovery of copper from the ore is at least 85 wt. %.

Embodiment 10 is the process of any of embodiments 1 to 9, wherein the metal comprises molybdenum, and a percent recovery of molybdenum from the ore is at least 75 wt. %.

Embodiment 11 is the process of any of embodiments 1 to 10, wherein during the step of contacting, the sulfur-containing compounds are present in a range from about 4.5 grams to about 50 grams per metric ton of ore.

Embodiment 12 is the process of any of embodiments 1 to 11, wherein the ore is in the form of ore particles in the step of contacting.

Embodiment 13 is the process of any of embodiments 1 to 12, wherein the ore comprises a copper-bearing ore, a molybdenum-bearing ore, or both a copper-bearing ore and a molybdenum-bearing ore.

Embodiment 14 is a collector composition comprising sulfur-containing compounds, the sulfur-containing compounds comprising (i) mercaptans comprising branched $C_{10}$ mercaptans compounds selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (ii) sulfides comprising branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

Embodiment 15 is the collector composition of embodiment 14, wherein the sulfur-containing compounds are present in an amount of less than 0.1 wt. % based on a combined total weight of the collector composition and the ore.

Embodiment 16 is the collector composition of any of embodiments 14 to 15, wherein the sulfur-containing compounds comprise from about 15 wt. % to about 80 wt. % sulfides, and wherein the sulfides are the branched $C_{20}$ sulfides.

Embodiment 17 is the collector composition of any of embodiments 14 to 16, wherein the branched $C_{10}$ mercaptans are present in an amount of at least about 50 wt. % based on a total weight of the mercaptans in the collector composition.

Embodiment 18 is the collector composition of any of embodiments 14 to 17, wherein the branched $C_{20}$ sulfides are present in an amount of at least 50 wt. % based on a total weight of the sulfides in the collector composition.

Embodiment 19 is the collector composition of any of embodiments 14 to 18, further comprising water, a pH control agent, a frothing agent, a hydrocarbon, an oily reagent, a water immiscible liquid, or combinations thereof.

Embodiment 20 is the collector composition of any of embodiments 14 to 19, further comprising a second collector agent.

Embodiment 21 is the collector composition of embodiment 20, wherein the second collector agent is xanthate, a xanthic ester, a thionocarbonate, a dialkyl dithiophosphate, or combinations thereof.

Embodiment 22 is the collector composition of any of embodiments 14 to 21, wherein the sulfur-containing compounds of the collector composition have an odor which is less unpleasant than an odor of mercaptan compounds which are n-decyl mercaptans, n-dodecyl mercaptans, tert-dodecyl mercaptans, or combinations thereof present in an amount of equal to or greater than about 25 wt. % of the mercaptan compounds in an otherwise similar mining collector composition.

Embodiment 23 is the process of any of embodiments 1 to 13, wherein the sulfur-containing compounds of the collector composition have an odor which is less unpleasant than an odor of mercaptan compounds which are n-decyl mercaptans, n-dodecyl mercaptans, tert-dodecyl mercaptans, or combinations thereof present in an amount of equal to or greater than about 25 wt. % of the mercaptan compounds in an otherwise similar mining collector composition.

Embodiment 24 is the process of any of embodiments 1 to 13 and 23, wherein the collector composition further comprises a second collector agent.

Embodiment 25 is the process of any of embodiments 23 to 24, wherein the second collector agent is xanthate, a xanthic ester, a thionocarbonate, a dialkyl dithiophosphate, or combinations thereof.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A mining chemical collector composition comprising sulfur-containing compounds, the sulfur-containing compounds comprising:
   (i) mercaptans comprising branched $C_{10}$ mercaptans compounds selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and
   (ii) sulfides comprising branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

2. The collector composition of claim 1, wherein the sulfur-containing compounds are present in an amount of less than 0.1 wt. % based on a combined total weight of the collector composition and ore.

3. The collector composition of claim 1, wherein the sulfur-containing compounds comprise from about 15 wt. % to about 80 wt. % sulfides, and wherein the sulfides are the branched $C_{20}$ sulfides.

4. The collector composition of claim 1, wherein the branched $C_{10}$ mercaptans are present in an amount of at least about 50 wt. % based on a total weight of the mercaptans in the collector composition.

5. The collector composition of claim 1, wherein the branched $C_{20}$ sulfides are present in an amount of at least 50 wt. % based on a total weight of the sulfides in the collector composition.

6. The collector composition of claim 1, further comprising water, a pH control agent, a frothing agent, a hydrocarbon, an oily reagent, a water immiscible liquid, or combinations thereof.

7. The collector composition of claim 1, further comprising a second collector agent.

8. The collector composition of claim 7, wherein the second collector agent is xanthate, a xanthic ester, a thionocarbonate, a dialkyl dithiophosphate, or combinations thereof.

9. The collector composition of claim 1, wherein the sulfur-containing compounds of the collector composition have an odor which is less unpleasant than an odor of mercaptan compounds which are n-decyl mercaptans, n-dodecyl mercaptans, tert-dodecyl mercaptans, or combinations thereof present in an amount of equal to or greater than about 25 wt. % of the mercaptan compounds in an otherwise similar mining collector composition.

10. A metal flotation mixture comprising metal-containing ore and the collector composition of claim 1.

11. The mixture of claim 10, wherein the sulfur-containing compounds are present in an amount of less than 0.1 wt. % based on a combined total weight of the collector composition and the ore.

12. The mixture of claim 10, wherein the sulfur-containing compounds are present in a range from about 4.5 grams to about 50 grams per metric ton of ore.

13. The mixture of claim 10, wherein the metal comprises gold, silver, platinum, copper, nickel, iron, lead, zinc, molybdenum, cobalt, chromium, or combinations thereof.

14. The mixture of claim 10, wherein the ore comprises a copper-bearing ore, a molybdenum-bearing ore, or both a copper-bearing ore and a molybdenum-bearing ore.

15. The mixture of claim 10, further comprising water and a frothing agent.

16. The mixture of claim 15 further comprising a pH control agent, a hydrocarbon, an oily reagent, a water immiscible liquid, or combinations thereof.

17. The mixture of claim 15, wherein the ore is in the form of ground ore particles.

18. The mixture of claim 10, wherein the sulfur-containing compounds of the mixture have an odor which is less unpleasant than an odor of mercaptan compounds which are n-decyl mercaptans, n-dodecyl mercaptans, tert-dodecyl mercaptans, or combinations thereof present in an amount of equal to or greater than about 25 wt. % of the mercaptan compounds in an otherwise similar metal flotation mixture.

19. A mining chemical collector composition comprising mercaptans, wherein at least about 50 wt. % of the mercaptans are 1) branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), and combinations thereof; and 2) 5-methyl-5-mercapto-nonane (represented by Structure H):

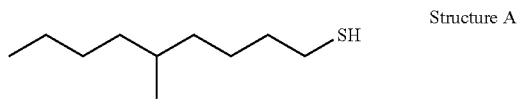

Structure A

-continued
Structure B
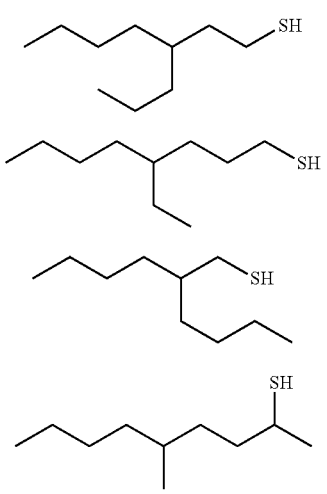
Structure C
Structure D
Structure E
-continued
Structure F
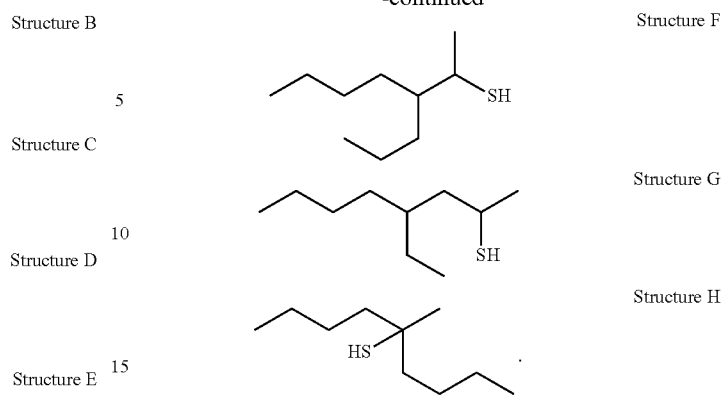
Structure G
Structure H
20. A metal flotation mixture comprising the mining chemical collector composition of claim 19.
* * * * *

UNITED STATES PATENT AND TRADEMARK OFFICE
CERTIFICATE OF CORRECTION

PATENT NO.       : 9,527,090 B1
APPLICATION NO.  : 15/284809
DATED            : December 27, 2016
INVENTOR(S)      : Jim D. Byers, Michael S. Matson and Jason L. Kreider Page 1 of 2

It is certified that error appears in the above-identified patent and that said Letters Patent is hereby corrected as shown below:

In the Specification

Table 2, Column 41 and Column 42, Lines 26 to the end of the page, should read:

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

TABLE 2
Structures of Mixed Decene Olefins and Mercaptan Reaction Products

| Decene Fraction | Olefin | Major UV Product | Major Acid Catalyst Product |
|---|---|---|---|
| 5-methyl-1-nonene 32.14% (38.19) | | | |
| 3-propyl-1-heptene 14.56% (17.23) | | | |
| 4-ethyl-1-octene 13.13% (15.60) | | | |
| 2-butyl-1-hexene 9.96% (11.83) | | | |
| 4/5 decene 9.12% (10.83) | | | |
| 1-decene 4.06% (4.85) | | | |